United States Patent [19]
Morser et al.

[11] Patent Number: 5,864,018
[45] Date of Patent: Jan. 26, 1999

[54] ANTIBODIES TO ADVANCED GLYCOSYLATION END-PRODUCT RECEPTOR POLYPEPTIDES AND USES THEREFOR

[75] Inventors: Michael John Morser, San Francisco; Mariko Nagashima, Belmont, both of Calif.

[73] Assignee: Schering Aktiengesellschaft, Berlin, Germany

[21] Appl. No.: 633,148

[22] Filed: Apr. 16, 1996

[51] Int. Cl.$^6$ .................................................. C07K 16/00
[52] U.S. Cl. ................................... 530/387.1; 530/387.3; 530/388.1; 530/388.22; 530/391.3
[58] Field of Search ............................ 530/387.1, 387.3, 530/388.1, 388.225, 391.3

[56] References Cited

U.S. PATENT DOCUMENTS 5,316,754  5/1994  Vlassera et al. ............................ 424/2

FOREIGN PATENT DOCUMENTS

| 45665 | 8/1981 | European Pat. Off. . |
| 0386752 | 12/1990 | European Pat. Off. . |
| 93 04086 | 4/1993 | WIPO . |

OTHER PUBLICATIONS

Neeper, M. et al. 1992. J. Biol. Clear. 267(21): 14998–15004.

Schmidt, A M et al. 1993 J. Clin. Invest 92: 2155–2168

Williams, G. 1988. TIBTECH, 6: 34–42.

Brownlee, "Advanced Protein Glycosylation in Diabetes and Aging," *Ann. Rev. Med.,* 46:223–234 (1995).

Doi et al., "Receptor-specific increase in extracellular matrix production in mouse mesangial cells by advanced glycosylation end products is medated via platelet–derived growth factor," *PNAS,* 89:2873–2877 (1992).

Esposito et al., "Endothelial Receptor-Mediated Binding of Glucose–Modified Albumin is Associated with Increased Monolayer Permeability and Modulation of Cell Surface Coagulant Properties,"*J. Exp. Med.,* 170:1387–1407 (1989).

Li et al., "Antibacterial activity of lysozyme and lactoferrin is inhibited by binding of advanced glycation–modified proteins to a conserved motif," *Nature Med.,* 1(10): 1057–1061 (1995).

Miyata et al., "Involvement of $\beta_2$–Microglobulin Modified with Advanced Glycation End Products in the Pathogenesis of Hemodialysis–associated Amuloidosis," *J. Clin. Invest.,* 93:521–528 (1994).

Radoff et al., "Isolation of Surface Binding Protein Specific for Advanced Glycosylation End Products From Mouse Macrophage–Derived Cell Line RAW 264.7," *Diabetes,* 39:1510–1518 (1990).

Schmidt et al., "The Endothelial Cell Binding Site for Advanced Glycation End Products Consists of a Complex: An Integral Membrane Proteing and 9 lactoferrin–like Polypeptide," *J. Biol. Chem.,* 269:9882–9888 (1994).

Skolnick et al., "Human and Rat Mesangial Cell Receptors for Glucose–modified Proteins: Potential Role in Kidney Tissue Remodelling and Diabetic Nephropathy," *J. Exp. Med.,* 174:931–939 (1991).

Smith et al., "Advanced Maillard reaction end products are associated with Alzheimer disease pathology," *PNAS,* 91:5710–5714 (1994).

Smith et al., "Early AGEing and Alzheimer's," *Nature,* 374:316 (1995).

Takata et al., "Endocytic Uptake of Nonenzymatically Glycosylated Proteins is Mediated by Scavenger Receptor for Aldehyde–modified Proteins," *J. Biol. Chem.,* 263:14819–14825 (1988).

Takata et al., "Scavenger receptor of human monocytic leukemia cell line (THP–11) and murine macrophages for nonenzymaticall glycosylated proteins," *Biochim. Biophys. Acta,* 986:18–26 (1989).

Vlassara et al., "Chachectin/TNF and IL–1 Induced by Glucose–Modified Proteins: Role in Normal Tissue Remodeling," *Science,* 240:1546–1548 (1988).

Vlassara et al., "Biology of Disease. Pathogenic Effects of Advanced Glycosylation: Biochemical, Biologic, and Clinical Implications for Diabetes and Aging," *Laboratory Invest.,* 70(2): 138–151 (1994).

Vlassara et al., Advanced glycation end products induce flomerular sclerosis and albuminuria in normal rats, *PNAS,* 91:11704–11708 (1994).

Yan et al., "Enhanced Ceullular Oxidant Stree by the Interaction of Advanced Glycation End Products with Their Receptors/Binding Proteins," *J. Biol. Chem.,* 269–9889–9897 (1994).

Zimmerman et al., Neurotoxicity of advanced glycation endproducts during focal stroke and neuroprotective effects of aminoguanidine, *PNAS,* 92:3744–3748 (1995).

Vissing, Henrik et al.; "Localization of the Human Gene for Advanced Glycosylation End Product–Specific Receptor (AGER) to Chromosome 6p21.3"; *Genomics;* 24:606–608 (1994).

Schmidt Ann Marie et al.; "RAGE–A Novel Cellular Receptor for Advanced Glycation End Porducts"; *Diabetes;* 45(suppl 3);s77–s80; (Jul. 1996).

Abel, M. et al.; "Expression of receptors for advanced glycosylated end–products in renal disease"; *Nephrology Dialysis Transplantation;* 10(9): 1662–1667; (1995).

(List continued on next page.)

*Primary Examiner*—Lila Feisee
*Assistant Examiner*—Minh-Tam Davis
*Attorney, Agent, or Firm*—Townsend and Townsend and Crew LLP

[57] ABSTRACT

It is a general object of the present invention to provide compositions that specifically interact with advanced glycosylation end products (AGEs) or their receptors. Such compositions may be used in a variety of applications including therapeutic applications, e.g., as blocking agents to inhibit or otherwise reduce the AGE/RAGE interaction, screening applications, e.g., as models of the AGE/RAGE interaction, and diagnostic applications, e.g., to identify abnormal levels of AGE or RAGE in a given system.

10 Claims, 25 Drawing Sheets

OTHER PUBLICATIONS

Ritthaler, U. et al.; "Expression of Receptors for Advanced Glycation End Products in Peripheral Occlusive Vascular Disease"; *American Journal of Pathology;* 146(3):688–694; (1995).

Schmidt, Ann Marie et al.; "Isolation and Characterization of Two Binding Proteins for Advanced Glycosylation End Products from Bovino Lung Which Are Present on the Endothelial Cell Surface"; *Journal of Biological Chemistry;* 267:14987–14997; (1992).

Li, Yong Ming et al.; "Molecular identity and cellular distribution of advanced glycation endproduct receptors: Relationship of p60 to OST–48 and p90 to 80K–H membrane proteins", *Proc. Natl. Acad. Sci. USA;* 93:11047–11052; (Oct. 1996).

Yang, Zhi et al.; "Two Novel Rat Liver Membrane Proteins that Bind Advanced Glycosylation Endproducts: Relationship to Macrophase Receptor for Glucose–modified Proteins"; *J. Exp. Med.;* 174:515–524; (Sept. 1991).

Brett, Jerold et al.; "Survey of the Distribution of a Newly Characterized Receptor for Advanced Glycation End Products in Tissues"; *American Journal of Pathology;* 143(6): 1699–1712; (Dec. 1993).

Wautier, et al.; "Advanced Glycation End Products (AGES) On The Surface Of Diabetic Erythrocytes Bind To The Vessel Wall Via A Specific Receptor Inducing Oxidant Stress In The Vasculature: A Link Between Surface–Associated AGES And Diabetic Complications"; *Proceedings of the National Academy of Sciences, USA;* 91:7742–7746; (Aug. 1994).

Hori et al.; "The Receptor For Advanced Glycation End Products (RAGE) is a Cellular Binding Site For Amphoterin. Mediation Of Neurite Outgrowth And Co–Expression Of Rage Amphoterin In The Developing Nervous System"; *The Journal of Biological Chemistry,* 270(43):25752–25761; (Oct. 1995).

Vlassera; "AGE–Receptors and In Vivo Biological Effects of AGES"; *Spec. Publ. –R Soc. Chem;* 151:254–261 (1994).

Imani, et al.; "Advanced Glycosylation Endproduct–Specific Receptors On Human And Rat T–Lymphocytes Mediate Synthesis Of Interferon Gamma; Role In Tissue Remodelling"; *Journal of Experimental Medicine;* 178(6); 2165–2172 (1993).

Hori, et al.; "The Receptor For Advanced Glycation End–Products Has A Central Role In Mediating The Effects Of Advanced Glycation End–Products On The Development Of Vascular Disease In Diabetes Mellitus"; *Nephrology, Dialysis, Transplantation;* 11(s5):13–16 (1996).

Sugaya, Kimihiko et al.; "Three Genes in the Human MHC Class III Region near the Junction with the Class II: Gene for Receptor of Advanced Glycosylation End Products, PBX2 Homeobox Gene and a Notch Homolog, Human Counterpart of Mouse Mammary Tumor Gene *int–3*"; *Genomics:* 23:408–419 (1994).

Harris, E.L.V. et al.; "Clarificaton and Extraction"; *Protein Purificaton Methods: A Practical Approach;* IRL Press, Oxford, UK; 67–69 (1989).

```
    MetAlaAlaGlyThrAlaValGlyAlaTrpValLeuValLeuSerLeuTrpGlyAlaVal
  1 ATGGCAGCCGGAACAGCAGTTGGAGCCTGGGTGCTGGTCCTCAGTCTGTGGGGGCAGTA

ValGlyAlaGlnAsnIleThrAlaArgIleGlyGluProLeuValLeuLysCysLysGly
 61 GTAGGTGCTCAAAACATCACAGCCCGGATTGGCGAGCCACTGGTGCTGAAGTGTAAGGGG

AlaProLysLysProProGlnArgLeuGluTrpLysLeuAsnThrGlyArgThrGluAla
121 GCCCCCAAGAAACCACCCCAGCGGCTGGAATGGAAACTGAACACAGGCCGGACAGAAGCT

TrpLysValLeuSerProGlnGlyGlyGlyProTrpAspSerValAlaArgValLeuPro
181 TGGAAGGTCCTGTCTCCCCAGGGAGGAGGCCCCTGGGACAGTGTGGCTCGTGTCCTTCCC

AsnGlySerLeuPheLeuProAlaValGlyIleGlnAspGluGlyIlePheArgCysGln
241 AACGGCTCCCTCTTCCTTCCGGCTGTCGGGATCCAGGATGAGGGGATTTTCCGGTGCCAG

AlaMetAsnArgAsnGlyLysGluThrLysSerAsnTyrArgValArgValTyrGlnIle
301 GCAATGAACAGGAATGGAAAGGAGACCAAGTCCAACTACCGAGTCCGTGTCTACCAGATT

ProGlyLysProGluIleValAspSerAlaSerGluLeuThrAlaGlyValProAsnLys
361 CCTGGGAAGCCAGAAATTGTAGATTCTGCCTCTGAACTCACGGCTGGTGTTCCCAATAAG

ValGlyThrCysValSerGluGlySerTyrProAlaGlyThrLeuSerTrpHisLeuAsp
421 GTGGGGACATGTGTGTCAGAGGGAAGCTACCCTGCAGGGACTCTTAGCTGGCACTTGGAT

GlyLysProLeuValProAsnGluLysGlyValSerValLysGluGlnThrArgArgHis
481 GGGAAGCCCCTGGTGCCTAATGAGAAGGGAGTATCTGTGAAGGAACAGACCAGGAGACAC

ProGluThrGlyLeuPheThrLeuGlnSerGluLeuMetValThrProAlaArgGlyGly
541 CCTGAGACAGGGCTCTTCACACTGCAGTCGGAGCTAATGGTGACCCCAGCCCGGGGAGGA

AspProArgProThrPheSerCysSerPheSerProGlyLeuProArgHisArgAlaLeu
601 GATCCCCGTCCCACCTTCTCCTGTAGCTTCAGCCCAGGCCTTCCCCGACACCGGGCCTTG

ArgThrAlaProIleGlnProArgValTrpGluProValProLeuGluGluValGlnLeu
661 CGCACAGCCCCCATCCAGCCCCGTGTCTGGGAGCCTGTGCCTCTGGAGGAGGTCCAATTG

ValValGluProGluGlyGlyAlaValAlaProGlyGlyThrValThrLeuThrCysGlu
721 GTGGTGGAGCCAGAAGGTGGAGCAGTAGCTCCTGGTGGAACCGTAACCCTGACCTGTGAA

ValProAlaGlnProSerProGlnIleHisTrpMetLysAspGlyValProLeuProLeu
781 GTCCCTGCCCAGCCCTCTCCTCAAATCCACTGGATGAAGGATGGTGTGCCCTTGCCCCTT

ProProSerProValLeuIleLeuProGluIleGlyProGlnAspGlnGlyThrTyrSer
841 CCCCCCAGCCCTGTGCTGATCCTCCCTGAGATAGGGCCTCAGGACCAGGGAACCTACAGC

CysValAlaThrHisSerSerHisGlyProGlnGluSerArgAlaValSerIleSerIle
901 TGTGTGGCCACCCATTCCAGCCACGGGCCCCAGGAAAGCCGTGCTGTCAGCATCAGCATC

IleGluProGlyGluGluGlyProThrAlaGlySerValGlyGlySerGlyLeuGlyThr
961 ATCGAACCAGGCGAGGAGGGGCCAACTGCAGGCTCTGTGGGAGGATCAGGGCTGGGAACT

OP
1021 TGA                        FIG. IA.
```

```
    AlaGlnAsnIleThrAlaArgIleGlyGluProLeuValLeuLysCysLysGlyAlaPro
  1 GCTCAAAACATCACAGCCCGGATTGGCGAGCCACTGGTGCTGAAGTGTAAGGGGGCCCCC

LysLysProProGlnArgLeuGluTrpLysLeuAsnThrGlyArgThrGluAlaTrpLys
 61 AAGAAACCACCCCAGCGGCTGGAATGGAAACTGAACACAGGCCGGACAGAAGCTTGGAAG

ValLeuSerProGlnGlyGlyGlyProTrpAspSerValAlaArgValLeuProAsnGly
121 GTCCTGTCTCCCCAGGGAGGAGGCCCCTGGGACAGTGTGGCTCGTGTCCTTCCCAACGGC

SerLeuPheLeuProAlaValGlyIleGlnAspGluGlyIlePheArgCysGlnAlaMet
181 TCCCTCTTCCTTCCGGCTGTCGGGATCCAGGATGAGGGGATTTTCCGGTGCCAGGCAATG

AsnArgAsnGlyLysGluThrLysSerAsnTyrArgValArgValTyrGlnIleProGly
241 AACAGGAATGGAAAGGAGACCAAGTCCAACTACCGAGTCCGTGTCTACCAGATTCCTGGG

LysProGluIleValAspSerAlaSerGluLeuThrAlaGlyValProAsnLysValGly
301 AAGCCAGAAATTGTAGATTCTGCCTCTGAACTCACGGCTGGTGTTCCCAATAAGGTGGGG

ThrCysValSerGluGlySerTyrProAlaGlyThrLeuSerTrpHisLeuAspGlyLys
361 ACATGTGTGTCAGAGGGAAGCTACCCTGCAGGGACTCTTAGCTGGCACTTGGATGGGAAG

ProLeuValProAsnGluLysGlyValSerValLysGluGlnThrArgArgHisProGlu
421 CCCCTGGTGCCTAATGAGAAGGGAGTATCTGTGAAGGAACAGACCAGGAGACACCCTGAG

ThrGlyLeuPheThrLeuGlnSerGluLeuMetValThrProAlaArgGlyGlyAspPro
481 ACAGGGCTCTTCACACTGCAGTCGGAGCTAATGGTGACCCCAGCCCGGGGAGGAGATCCC

ArgProThrPheSerCysSerPheSerProGlyLeuProArgHisArgAlaLeuArgThr
541 CGTCCCACCTTCTCCTGTAGCTTCAGCCCAGGCCTTCCCCGACACCGGGCCTTGCGCACA

AlaProIleGlnProArgValTrpGluProValProLeuGluGluValGlnLeuValVal
601 GCCCCCATCCAGCCCCGTGTCTGGGAGCCTGTGCCTCTGGAGGAGGTCCAATTGGTGGTG

GluProGluGlyGlyAlaValAlaProGlyGlyThrValThrLeuThrCysGluValPro
661 GAGCCAGAAGGTGGAGCAGTAGCTCCTGGTGGAACCGTAACCCTGACCTGTGAAGTCCCT

AlaGlnProSerProGlnIleHisTrpMetLysAspGlyValProLeuProLeuProPro
721 GCCCAGCCCTCTCCTCAAATCCACTGGATGAAGGATGGTGTGCCCTTGCCCCTTCCCCCC

SerProValLeuIleLeuProGluIleGlyProGlnAspGlnGlyThrTyrSerCysVal
781 AGCCCTGTGCTGATCCTCCCTGAGATAGGGCCTCAGGACCAGGGAACCTACAGCTGTGTG

AlaThrHisSerSerHisGlyProGlnGluSerArgAlaValSerIleSerIleIleGlu
841 GCCACCCATTCCAGCCACGGCCCCAGGAAAGCCGTGCTGTCAGCATCAGCATCATCGAA

ProGlyGluGluGlyProThrAlaGlySerValGlyGlySerGlyLeuGlyThrOP
901 CCAGGCGAGGAGGGGCCAACTGCAGGCTCTGTGGGAGGATCAGGGCTGGGAACTTGA
```

FIG. IB.

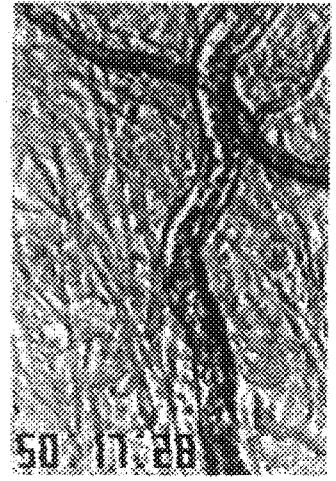
FIG. 15A.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 1023 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
ATGGCAGCCG  GAACAGCAGT  TGGAGCCTGG  GTGCTGGTCC  TCAGTCTGTG  GGGGGCAGTA        60
```

| | | | | | |
|---|---|---|---|---|---|
| GTAGGTGCTC | AAAACATCAC | AGCCCGGATT | GGCGAGCCAC | TGGTGCTGAA | GTGTAAGGGG | 120 |
| GCCCCCAAGA | AACCACCCCA | GCGGCTGGAA | TGGAAACTGA | ACACAGGCCG | GACAGAAGCT | 180 |
| TGGAAGGTCC | TGTCTCCCCA | GGGAGGAGGC | CCCTGGGACA | GTGTGGCTCG | TGTCCTTCCC | 240 |
| AACGGCTCCC | TCTTCCTTCC | GGCTGTCGGG | ATCCAGGATG | AGGGGATTTT | CCGGTGCCAG | 300 |
| GCAATGAACA | GGAATGGAAA | GGAGACCAAG | TCCAACTACC | GAGTCCGTGT | CTACCAGATT | 360 |
| CCTGGGAAGC | CAGAAATTGT | AGATTCTGCC | TCTGAACTCA | CGGCTGGTGT | TCCCAATAAG | 420 |
| GTGGGGACAT | GTGTGTCAGA | GGGAAGCTAC | CCTGCAGGGA | CTCTTAGCTG | CACTTGGAT | 480 |
| GGGAAGCCCC | TGGTGCCTAA | TGAGAAGGGA | GTATCTGTGA | AGGAACAGAC | CAGGAGACAC | 540 |
| CCTGAGACAG | GGCTCTTCAC | ACTGCAGTCG | GAGCTAATGG | TGACCCCAGC | CCGGGGAGGA | 600 |
| GATCCCCGTC | CCACCTTCTC | CTGTAGCTTC | AGCCCAGGCC | TTCCCCGACA | CCGGGCCTTG | 660 |
| CGCACAGCCC | CCATCCAGCC | CCGTGTCTGG | GAGCCTGTGC | CTCTGGAGGA | GGTCCAATTG | 720 |
| GTGGTGGAGC | CAGAAGGTGG | AGCAGTAGCT | CCTGGTGGAA | CCGTAACCCT | GACCTGTGAA | 780 |
| GTCCCTGCCC | AGCCCTCTCC | TCAAATCCAC | TGGATGAAGG | ATGGTGTGCC | CTTGCCCCTT | 840 |
| CCCCCCAGCC | CTGTGCTGAT | CCTCCCTGAG | ATAGGGCCTC | AGGACCAGGG | AACCTACAGC | 900 |
| TGTGTGGCCA | CCCATTCCAG | CCACGGGCCC | CAGGAAAGCC | GTGCTGTCAG | CATCAGCATC | 960 |
| ATCGAACCAG | GCGAGGAGGG | GCCAACTGCA | GGCTCTGTGG | GAGGATCAGG | GCTGGGAACT | 1020 |
| TGA | | | | | | 1023 |

( 2 ) INFORMATION FOR SEQ ID NO:2:

( i ) SEQUENCE CHARACTERISTICS:
        ( A ) LENGTH: 340 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Ala | Ala | Gly | Thr<br>5 | Ala | Val | Gly | Ala | Trp<br>10 | Val | Leu | Val | Leu<br>15 | Ser | Leu |
| Trp | Gly | Ala | Val<br>20 | Val | Gly | Ala | Gln | Asn<br>25 | Ile | Thr | Ala | Arg | Ile<br>30 | Gly | Glu |
| Pro | Leu | Val<br>35 | Leu | Lys | Cys | Lys | Gly<br>40 | Ala | Pro | Lys | Lys | Pro<br>45 | Pro | Gln | Arg |
| Leu | Glu<br>50 | Trp | Lys | Leu | Asn | Thr<br>55 | Gly | Arg | Thr | Glu | Ala<br>60 | Trp | Lys | Val | Leu |
| Ser<br>65 | Pro | Gln | Gly | Gly | Gly<br>70 | Pro | Trp | Asp | Ser | Val<br>75 | Ala | Arg | Val | Leu | Pro<br>80 |
| Asn | Gly | Ser | Leu | Phe<br>85 | Leu | Pro | Ala | Val | Gly<br>90 | Ile | Gln | Asp | Glu | Gly<br>95 | Ile |
| Phe | Arg | Cys | Gln<br>100 | Ala | Met | Asn | Arg | Asn<br>105 | Gly | Lys | Glu | Thr | Lys<br>110 | Ser | Asn |
| Tyr | Arg | Val<br>115 | Arg | Val | Tyr | Gln | Ile<br>120 | Pro | Gly | Lys | Pro | Glu<br>125 | Ile | Val | Asp |
| Ser | Ala<br>130 | Ser | Glu | Leu | Thr | Ala<br>135 | Gly | Val | Pro | Asn | Lys<br>140 | Val | Gly | Thr | Cys |
| Val<br>145 | Ser | Glu | Gly | Ser | Tyr<br>150 | Pro | Ala | Gly | Thr | Leu<br>155 | Ser | Trp | His | Leu | Asp<br>160 |
| Gly | Lys | Pro | Leu | Val<br>165 | Pro | Asn | Glu | Lys | Gly<br>170 | Val | Ser | Val | Lys | Glu<br>175 | Gln |

```
        Thr  Arg  Arg  His  Pro  Glu  Thr  Gly  Leu  Phe  Thr  Leu  Gln  Ser  Glu  Leu
                       180                      185                      190

Met  Val  Thr  Pro  Ala  Arg  Gly  Gly  Asp  Pro  Arg  Pro  Thr  Phe  Ser  Cys
                       195                      200                      205

Ser  Phe  Ser  Pro  Gly  Leu  Pro  Arg  His  Arg  Ala  Leu  Arg  Thr  Ala  Pro
                       210                      215                      220

Ile  Gln  Pro  Arg  Val  Trp  Glu  Pro  Val  Pro  Leu  Glu  Glu  Val  Gln  Leu
        225                      230                      235                           240

Val  Val  Glu  Pro  Glu  Gly  Gly  Ala  Val  Ala  Pro  Gly  Gly  Thr  Val  Thr
                       245                      250                      255

Leu  Thr  Cys  Glu  Val  Pro  Ala  Gln  Pro  Ser  Pro  Gln  Ile  His  Trp  Met
                       260                      265                      270

Lys  Asp  Gly  Val  Pro  Leu  Pro  Leu  Pro  Pro  Ser  Pro  Val  Leu  Ile  Leu
                       275                      280                      285

Pro  Glu  Ile  Gly  Pro  Gln  Asp  Gln  Gly  Thr  Tyr  Ser  Cys  Val  Ala  Thr
                       290                      295                      300

His  Ser  Ser  His  Gly  Pro  Gln  Glu  Ser  Arg  Ala  Val  Ser  Ile  Ser  Ile
        305                      310                      315                           320

Ile  Glu  Pro  Gly  Glu  Gly  Pro  Thr  Ala  Gly  Ser  Val  Gly  Gly  Ser
                            325                      330                      335

Gly  Leu  Gly  Thr
                       340
```

( 2 ) INFORMATION FOR SEQ ID NO:3:

( i ) SEQUENCE CHARACTERISTICS:
        ( A ) LENGTH: 957 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GCTCAAAACA   TCACAGCCCG   GATTGGCGAG   CCACTGGTGC   TGAAGTGTAA   GGGGGCCCCC    60
AAGAAACCAC   CCCAGCGGCT   GGAATGGAAA   CTGAACACAG   GCCGGACAGA   AGCTTGGAAG   120
GTCCTGTCTC   CCCAGGGAGG   AGGCCCCTGG   GACAGTGTGG   CTCGTGTCCT   TCCCAACGGC   180
TCCCTCTTCC   TTCCCCCTGT   CGGGATCCAG   GATGAGGGGA   TTTTCCGGTG   CCAGGCAATG   240
AACAGGAATG   GAAAGGAGAC   CAAGTCCAAC   TACCGAGTCC   GTGTCTACCA   GATTCCTGGG   300
AAGCCAGAAA   TTGTAGATTC   TGCCTCTGAA   CTCACGGCTG   GTGTTCCCAA   TAAGGTGGGG   360
ACATGTGTGT   CAGAGGGAAG   CTACCCTGCA   GGGACTCTTA   GCTGGCACTT   GGATGGGAAG   420
CCCCTGGTGC   CTAATGAGAA   GGGAGTATCT   GTGAAGGAAC   AGACCAGGAG   ACACCCTGAG   480
ACAGGGCTCT   TCACACTGCA   GTCGGAGCTA   ATGGTGACCC   CAGCCCGGGG   AGGAGATCCC   540
CGTCCCACCT   TCTCCTGTAG   CTTCAGCCCA   GGCCTTCCCC   GACACCGGGC   CTTGCGCACA   600
GCCCCCATCC   AGCCCCGTGT   CTGGGAGCCT   GTGCCTCTGG   AGGAGGTCCA   ATTGGTGGTG   660
GAGCCAGAAG   GTGGAGCAGT   AGCTCCTGGT   GGAACCGTAA   CCCTGACCTG   TGAAGTCCCT   720
GCCCAGCCCT   CTCCTCAAAT   CCACTGGATG   AAGGATGGTG   TGCCCTTGCC   CCTTCCCCCC   780
AGCCCTGTGC   TGATCCTCCC   TGAGATAGGG   CCTCAGGACC   AGGGAACCTA   CAGCTGTGTG   840
GCCACCCATT   CCAGCCACGG   GCCCCAGGAA   AGCCGTGCTG   TCAGCATCAG   CATCATCGAA   900
CCAGGCGAGG   AGGGGCCAAC   TGCAGGCTCT   GTGGGAGGAT   CAGGGCTGGG   AACTTGA      957
```

( 2 ) INFORMATION FOR SEQ ID NO:4:

( i ) SEQUENCE CHARACTERISTICS:
 ( A ) LENGTH: 318 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:4:

```
Ala Gln Asn Ile Thr Ala Arg Ile Gly Glu Pro Leu Val Leu Lys Cys
1               5                   10                  15
Lys Gly Ala Pro Lys Lys Pro Pro Gln Arg Leu Glu Trp Lys Leu Asn
            20              25                  30
Thr Gly Arg Thr Glu Ala Trp Lys Val Leu Ser Pro Gln Gly Gly Gly
        35                  40                  45
Pro Trp Asp Ser Val Ala Arg Val Leu Pro Asn Gly Ser Leu Phe Leu
    50                  55                  60
Pro Ala Val Gly Ile Gln Asp Glu Gly Ile Phe Arg Cys Gln Ala Met
65                  70                  75                  80
Asn Arg Asn Gly Lys Glu Thr Lys Ser Asn Tyr Arg Val Arg Val Tyr
                85                  90                  95
Gln Ile Pro Gly Lys Pro Glu Ile Val Asp Ser Ala Ser Glu Leu Thr
                100                 105                 110
Ala Gly Val Pro Asn Lys Val Gly Thr Cys Val Ser Glu Gly Ser Tyr
            115                 120                 125
Pro Ala Gly Thr Leu Ser Trp His Leu Asp Gly Lys Pro Leu Val Pro
    130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                165                 170                 175
Gly Gly Asp Pro Arg Pro Thr Phe Ser Cys Ser Phe Ser Pro Gly Leu
            180                 185                 190
Pro Arg His Arg Ala Leu Arg Thr Ala Pro Ile Gln Pro Arg Val Trp
        195                 200                 205
Glu Pro Val Pro Leu Glu Glu Val Gln Leu Val Val Glu Pro Glu Gly
    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
        275                 280                 285
Gln Glu Ser Arg Ala Val Ser Ile Ser Ile Ile Glu Pro Gly Glu Glu
    290                 295                 300
Gly Pro Thr Ala Gly Ser Val Gly Gly Ser Gly Leu Gly Thr
305                 310                 315
```

( 2 ) INFORMATION FOR SEQ ID NO:5:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear (i i) MOLECULE TYPE: peptide (x i) SEQUENCE DESCRIPTION: SEQ ID NO:5:

Cys Lys Gly Ala Pro Lys Lys Pro Pro Gln
1               5                   10

(2) INFORMATION FOR SEQ ID NO:6:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:6:

Trp Lys Leu Asn Thr Gly Arg Thr Glu Ala Cys
1               5                   10

(2) INFORMATION FOR SEQ ID NO:7:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:7:

Gly Pro Gln Asp Gln Gly Thr Tyr Ser Cys
1               5                   10

(2) INFORMATION FOR SEQ ID NO:8:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:8:

Trp Lys Leu Asn Thr Gly Arg Thr Glu Ala
1               5                   10

(2) INFORMATION FOR SEQ ID NO:9:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:9:

Cys Glu Val Pro Ala Gln Pro Ser Pro Gln Ile
1               5                   10

(2) INFORMATION FOR SEQ ID NO:10:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:10:

Cys Arg Ala Met Asn Gln Asn Gly Lys Glu Thr Lys Ser Asn
1               5                   10

(2) INFORMATION FOR SEQ ID NO:11:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:11:

Gly Pro Gln Asp Gln Gly Thr Tyr Ser Cys
1               5                   10

(2) INFORMATION FOR SEQ ID NO:12:

(i) SEQUENCE CHARACTERISTICS:
      (A) LENGTH: 15 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:12:

Ala Gln Asn Ile Thr Ala Arg Ile Gly Glu Pro Leu Val Leu Lys
1               5                   10                  15

(2) INFORMATION FOR SEQ ID NO:13:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:13:

Cys Lys Gly Ala Pro Lys Lys Pro Pro Gln
1               5                   10

(2) INFORMATION FOR SEQ ID NO:14:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:14:

Glu Gln Thr Arg Arg His Pro Glu Thr
1               5

(2) INFORMATION FOR SEQ ID NO:15:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:15:

Arg Gly Gly Asp Pro Arg Pro Thr Phe Ser Cys
1               5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:16:

Ser Pro Gly Leu Pro Arg His Arg Ala Leu
1               5                   10

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:17:

Ser Ser His Gly Pro Gln Glu Ser Arg Ala
1               5                   10

(2) INFORMATION FOR SEQ ID NO:18:

(i) SEQUENCE CHARACTERISTICS:
        (A) LENGTH: 16 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:18:

Ala Gln Asn Ile Thr Ala Arg Ile Gly Glu Pro Leu Val Leu Lys Cys
1               5                   10                  15

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:19:

Cys Glu Gln Thr Arg Arg His Pro Glu Thr
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:20:

Cys Ser Pro Gly Leu Pro Arg His Arg Ala Leu
1               5                   10

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:21:

Ser Ser His Gly Pro Gln Glu Ser Arg Ala Cys
1               5                   10

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:22:

GATGGCAGCC GGAACAGCAG TT                            22

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:23:

CTCAAGTTCC CAGCCCTGAT CCTC                          24

ANTIBODIES TO ADVANCED GLYCOSYLATION END-PRODUCT RECEPTOR POLYPEPTIDES AND USES THEREFOR

BACKGROUND OF THE INVENTION

Advanced glycosylation end-products of proteins (AGES) have been implicated in a variety of disorders including complications associated with diabetes and normal aging. AGEs are nonenzymatically glycosylated proteins which have been shown to accumulate in vascular tissue in aging and at an accelerated rate in individuals with diabetes. Particularly, AGEs result from the non-enzymatic, but concentration dependant interaction of glucose and other reducing sugars with amino groups on proteins to form glycosylated proteins termed Amadori adducts. Over time, these Amadori adducts undergo additional rearrangements, dehydrations and cross-linking with other proteins to accumulate as a family of complex structures referred to as AGEs.

AGEs have been shown to bind specifically in a saturable and reversible manner to cell surface receptors, including receptors expressed on the surface of endothelial cells and particularly those of the microvasculature, monocytes/macrophages, smooth muscle cells, mesengial cells and neurons.

Following binding to cell surface receptors, AGEs are taken up in vesicles and either degraded intracellularly or transported through the cells and deposited in the subendothelial matrix, where they accumulate. Esposito et al., J. Exp. Med. 170:1387–1407 (1989). In addition, chemotactic signals for monocytes, but not other white cells are released. These monocytes then adhere and diapedese through the endothelial cell layer. Kirstein et al., Proc. Nat'l Acad. Sci. USA 187:9010–9014 (1990).

AGEs also have been shown to cause proliferation of endothelial cells, which become more permeable and more thrombogenic, i.e., thrombomodulin is downregulated while tissue factor is upregulated. Esposito et al., J. Exp. Med. 170:1387–1407 (1989).

*Monocytes macrophages* can also take up AGEs through their receptors which are distinct from the acetyl-LDL receptors, but which may be related to the receptors for aldehyde-modified proteins. Takata et al., J. Biol. Chem. 263:14819–14825 (1988), Takata et al., Biochim. Biophys. Acta 986:18–26 (1989), Radoff et al., Diabetes 39:1510–1518 (1990). Binding of AGEs to monocytes in vitro leads to the induction of cytokines, TNF and IL-1, which then stimulate the release of a number of other growth factors responsible for cell proliferation, migration and matrix synthesis. Vlassara et al., Science 240:1546–1548 (1988). Increased synthesis of matrix proteins in response to AGEs binding has also been demonstrated for mesangial cells. Skolnick et al., J. Exp. Med. 174:931–939 (1991), Doi et al., Proc. Nat'l Acad. Sci. USA 89:2873–2877 (1992).

Evidence has indicated that the binding of AGEs to their receptors either directly or indirectly induces inflammatory responses in vessel walls, which can trigger or aggravate the pathogenesis of diabetic macro- or microangiopathy. For an overview of the effects of AGEs, see, e.g., Vlassara et al., Laboratory Invest. 70(2):138–151 (1994). Stern et al., J. Biol. Chem. 267:14998–15004 (1992) has reported similarities between RAGE proteins and the Ig superfamily molecules.

Because of the effects AGEs may have in the pathogenesis of a number of disorders, it would generally be desirable to provide compositions and methods to block or otherwise inhibit these effects, and particularly the interaction between AGEs and their cell surface receptors. The present invention meets these and a variety of other needs.

SUMMARY OF THE INVENTION

It is a general object of the present invention to provide novel polypeptides and antibodies, as well as methods of using these polypeptides and antibodies in screening, diagnostic and therapeutic applications.

In a first aspect, the present invention provides isolated antibodies that are specifically immunoreactive with a soluble human RAGE polypeptide. In particular, the antibodies of the invention will be specifically immunoreactive with a polypeptide having an amino acid sequence substantially homologous to the amino acid sequence shown in FIG. 1(SEQ ID NOS: 1–4), or immunologically active fragments thereof. The present invention also provides pharmaceutical compositions which include these antibodies.

The antibodies of the present invention may also be used in therapeutic applications. For example, in a further aspect, the present invention provides methods of treating a patient for symptoms of a disorder which are caused by an interaction between an AGE and its receptor. The methods comprise administering an effective amount of an antibody that is specifically immunoreactive with a soluble human RAGE polypeptide to the patient.

In an additional aspect, the antibodies of the present invention may be used as affinity probes. For example in an additional aspect, the antibodies of the invention may be used in methods for detecting a human RAGE polypeptide in a sample. The methods comprise contacting the sample with an isolated antibody that is specifically immunoreactive with a soluble human RAGE polypeptide, and determining whether the antibody specifically immunoreacts with a component of the sample.

In a related aspect, the invention provides methods of purifying human RAGE polypeptides from a mixture of proteins. For these methods, an antibody that is specifically immunoreactive with a soluble human RAGE polypeptide is immobilized on a solid support. The solid support is contacted with the mixture of proteins under conditions which will permit specific immunoreaction between the antibody and the human RAGE polypeptide. The solid support is washed to remove nonspecifically bound proteins and the RAGE polypeptide is eluted from the solid support in substantially pure form.

BRIEF DESCRIPTION OF THE DRAWINGS

FIGS. 1A and 1B show the nucleic acid sequence and deduced amino acid sequence of a soluble human RAGE polypeptide(SEQ ID NO: 1–4). FIG. 1A shows the DNA and amino acid sequence of soluble human RAGE which includes an expressed pre-sequence, whereas FIG. 1B shows the sequences (SEQ ID NO: 1–2) for mature soluble human RAGE (SEQ ID NO: 3–4). Standard three-letter abbreviations are used to denote the individual amino acids.

FIG. 2A shows total binding of labeled AGE-BSA to RAGE immobilized indirectly upon a solid support through a FLAG peptide/antiFLAG antibody interaction which mimics the cell surface presentation of RAGE (squares). Also shown is nonspecific binding (diamonds)(labeled AGE-BSA binding in the presence of excess unlabeled AGE-BSA). FIG. 2B shows corrected, specific binding of AGE-BSA to RAGE polypeptide that is indirectly coupled to the solid support.

FIG. 6A shows a capture assay employing MAb RBF9D9 (ATCC Accession No. HB-12165) as the RAGE capture antibody and MAb SW1OC1 (ATCC Accession No. HB-12164)as the RAGE detection antibody, which recognizes human, but not murine RAGE. FIG. 6B shows a capture assay employing MAb RBF9D9 (ATCC Accession No. HB-12165) as the RAGE capture antibody and MAb SW1E8 (ATCC Accession No. 12164) as the detection antibody, which recognizes both human and murine RAGE.

FIGS. 15A and 15B show adhesion of RAGE pretreated and control RBCs to single vessels.

DETAILED DESCRIPTION OF THE INVENTION

I. General

Figure 2A:
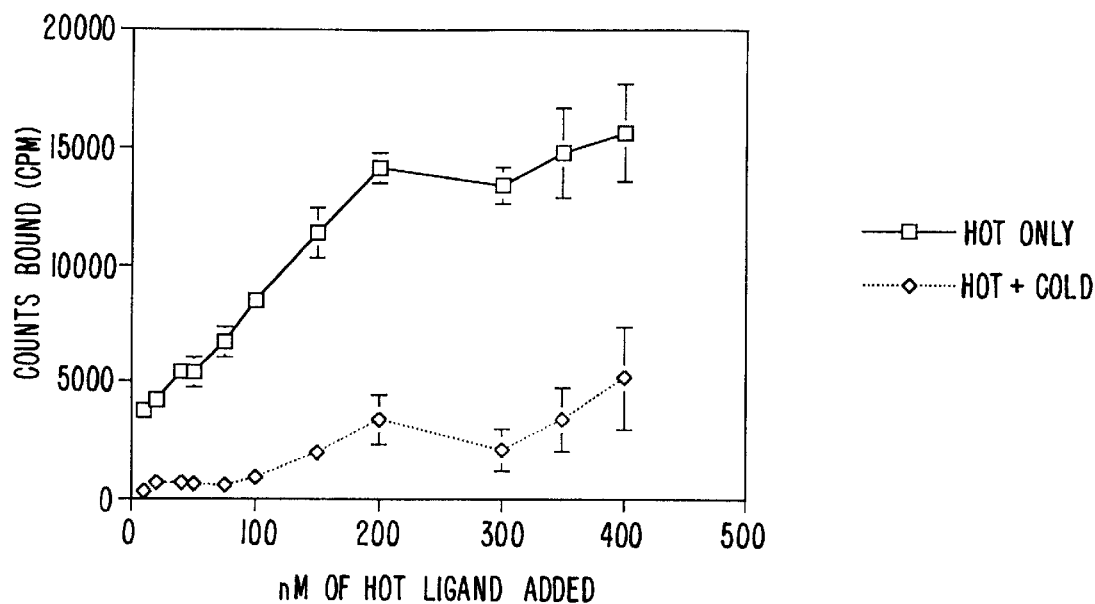
FIGS. 2A and 2B show binding of an AGE-BSA protein to indirectly immobilized RAGE polypeptide.

The major pathological conditions in which AGEs have been implicated as exerting adverse effects include Diabetes Mellitus in which hyperglycemia exists, as well as a number of aging related disorders. AGE formation in biological systems is dependant upon blood-glucose concentration and time of incubation. Without being bound to a particular theory, it is believed that this time/concentration dependency accounts for the adverse effects in hyperglycemic diabetics as well as the elderly. Similarly, proteins which themselves have a longer half-life, are more prone to undergo glycosylation to form AGEs. In diabetic patients, a high level of plasma glucose leads to glycosylation of various plasma proteins, including hemoglobin and LDL (low-density lipoprotein) as well as enzymes and matrix proteins. The accumulation of these AGEs induce a number of permanent abnormalities in the extracellular matrix component function, and stimulate cytokines and reactive oxygen species production through AGE-specific receptors. Inhibition of AGE formation in long term diabetic animals has also been shown to prevent or reduce the severity of a number of elements of the pathology of diabetes, including retinopathy, nephropathy, neuropathy and arterial abnormalities. Brownlee, Ann. Rev. Med. 46:223–234 (1995), Zimmerman et al., Proc. Nat'l Acad. Sci. USA 92:3744–3748 (1995).

A number of proteins associated with Alzheimer's disease, e.g., amyloid, tau, the major components of neurofibrillary tangles and senile plaques, are found to be similarly modified. Smith et al., Nature 374:316 (1995), Smith et al.,Proc. Nat'l Acad. Sci. USA, 91:5710–5714 (1994), Vitek et al., Proc. Nat'l Acad. Sci. USA, 91:4766–4770 (1994). Additionally, in hemodialysis-associated amyloidosis, $\beta_2$-microglobulin, a major component of amyloid fibrils, is modified by glycosylation. Miyata et al., J. Clin. Invest. 93:521–528 (1994). In atherosclerosis, in both the diabetic and non-diabetic populations, LDL, Lp(a)(lipoprotein little a) and immunoglobulin that are trapped and/or cross-linked to the matrix within the vessel wall are modified by glycosylation. The presence of AGEs produces a local, chronic inflammation, through a number of mechanisms including receptor-mediated pathway and oxidant stress. As a result, it is apparent that AGE modification causes and/or aggravates these various pathological conditions.

Because of these effects of AGEs in the pathogenesis of various disorders, it is a general object of the present invention to provide compositions that specifically interact with advanced glycosylation end products (AGEs) or their receptors. Such compositions may be used in a variety of applications including therapeutic applications, e.g., as blocking agents to inhibit or otherwise reduce the AGE/RAGE interaction, screening applications, e.g., as models of the AGE/RAGE interaction, and diagnostic applications, e.g., to identify abnormal levels of AGE or RAGE in a given system.

In preferred aspects, the present invention provides compositions comprising soluble RAGE polypeptides, antibodies that are specifically immunoreactive with soluble RAGE polypeptides, and methods of using these compositions in screening, therapeutic and diagnostic applications.

II. Polypeptides

In a first aspect, the present invention provides substantially pure or isolated polypeptides that are related to and/or derived from human RAGE polypeptides. The terms "substantially pure" or "isolated", when referring to proteins and polypeptides, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up from about 75 to about 90% of the total protein. Preferably, the protein will make up greater than about 90%, and more preferably, greater than about 95% of the total protein in the composition.

In particular aspects, the isolated polypeptides of the present invention are related to and/or derived from soluble human RAGE polypeptides. As used herein, the term "soluble" generally refers to RAGE derived polypeptides that lack a transmembrane region that is associated with full length RAGE polypeptides. Thus, soluble RAGE polypeptides generally comprise fragments of the extracellular domain of RAGE. In certain embodiments, the soluble peptides of the invention will comprise one or more of the Ig-like domains of the extracellular region of RAGE.

As used herein, "AGE" refers to an advanced glycosylation end-product. Typically, such AGEs may be full length proteins, polypeptides or aggregations of proteins and/or polypeptides.

The polypeptides of the invention also may be characterized by their ability to either mimic or inhibit the interaction between AGEs and their receptors, e.g., RAGE. Those polypeptides which are mimetic of either AGE or its receptors in the AGE/receptor interaction are termed AGE or AGE receptor "mimics".

In particularly preferred aspects, the polypeptides of the invention will have an amino acid sequence that is related to or derived from the amino acid sequence of soluble human RAGE as shown in FIGS. 1A and 1B (SEQ ID NOS: 1–4). Although described in terms of the amino acid sequence shown in FIG. 1A and 1B (SEQ ID NOS: 1–4), it will be readily understood that the polypeptides of the present invention include those peptides having the listed amino acid sequence or biologically active fragments thereof, as well as those polypeptides having amino acid sequences that are substantially homologous to the listed sequence.

The terms "substantially homologous" when referring to polypeptides, refer comparatively to two amino acid sequences which, when optimally aligned, are at least about 75% homologous, preferably at least about 85% homologous more preferably at least about 90% homologous, and still more preferably at least about 95% homologous. Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, WI).

The term "biologically active fragment" as used herein, refers to portions of the soluble RAGE polypeptides, which possess a particular biological activity. For example, such biological activity may include the ability to bind a particular protein, substrate or ligand, e.g., AGE, to have antibodies generated against it, to block or otherwise inhibit an interaction between two proteins, e.g., a receptor and its ligand, such as AGE and RAGE, between an enzyme and its substrate, between an epitope and an antibody, or such fragments may include a particular catalytic activity. With regard to the polypeptides of the present invention, particularly preferred polypeptides or biologically active fragments include, e.g., polypeptides that possess one or more of the biological activities described above, such as the ability to specifically interact with AGES, the ability to block, reduce, or otherwise inhibit the interaction between AGEs and RAGE, and the ability to elicit antibodies that are specifically immunoreactive with AGEs or RAGE. Those fragments that are specifically recognized and bound by antibodies raised against the polypeptides of the invention are also included in the definition of biologically active fragments. Such fragments are also referred to herein as "immunologically active fragments." Examples of immunologically active fragments include those fragments comprising the amino acid sequences specifically described below, and particularly those selected from the group consisting of: WKLNTGRTEA (SEQ ID NO: 8), CEVPAQPSPQI (SEQ ID NO: 9), CRAMNQNGKETKSN (SEQ ID NO: 10), GPQDQGTYSC (SEQ ID NO: 11), AQNITARIGEPLVLK (SEQ ID NO: 12), CKGAPKKPPQ (SEQ ID NO: 13), EQTRRHPET (SEQ ID NO: 14), RGGDPRPTFSC (SEQ ID NO: 15), SPGLPRHRAL (SEQ ID NO: 16), and SSHGPQESRA (SEQ ID NO: 17).

As described previously, the polypeptides of the invention may further include modifications to the N- or C-termini, i.e., acetylation, amidation, or inclusion of additional amino acids to assist in conjugation with other proteins or other compounds, e.g., polypeptides having the following sequences: WKLNTGRTEAC (SEQ ID NO: 6); AQNITARIGEPLVLKC (SEQ ID NO: 18); CEQTRRHPET (SEQ ID NO: 19); CSPGLPRHRAL (SEQ ID NO: 20); and SSHGPQESRAC (SEQ ID NO: 21).

The polypeptides of the invention may also be characterized by their ability to block the interaction between two proteins, e.g. AGE and RAGE, RAGE and anti-RAGE Abs, or AGE and anti-AGE Abs. In particular, included in the polypeptides of the present invention are peptides derived from human RAGE proteins that are capable of blocking or otherwise inhibiting the interaction between human RAGE and its ligands and particularly, AGEs. Examples of such polypeptides include fragments of human RAGE which encompass the AGE binding regions of the RAGE protein as well as AGE-binding proteins that sterically interfere with RAGE/AGE binding.

As referenced above, the polypeptides of the present invention may also be characterized by their ability to bind antibodies raised against proteins or polypeptides having the amino acid sequences of soluble human RAGE, as shown in FIG. 1A and 1B(SEQ ID NO: 1–4), or fragments thereof. These antibodies generally recognize polypeptides that are homologous to at least portions of human RAGE proteins or their immunologically active fragments. A variety of immunoassay formats may be used to select antibodies specifically immunoreactive with a particular protein or domain. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. Antibodies to the polypeptides of the present invention are discussed in greater detail, below.

Generally, the biologically active fragments of the polypeptides described herein may include any subsequence of the above described RAGE polypeptide. Typically, however, such biologically active fragments will range in size from about 10 amino acids in length to about 320 amino acids in length. More typically, the biologically active fragments will be from about 10, 11, 12, 13, 14, 15 or 16 amino acids in length to about 50 amino acids in length.

Examples of particularly preferred biologically active fragments of soluble human RAGE include peptides comprising an amino acid sequence selected from the group consisting of WKLNTGRTEA (SEQ ID NO: 8), CEVPAQPSPQI (SEQ ID NO: 9), CRAMNQNGKETKSN (SEQ ID NO: 10), GPQDQGTYSC (SEQ ID NO: 11), AQNITARIGEPLVLK (SEQ ID NO: 12), CKGAPKKPPQ (SEQ ID NO: 13), EQTRRHPET (SEQ ID NO: 14), RGGDPRPTFSC (SEQ ID NO: 15), SPGLPRHRAL (SEQ ID NO: 16), and SSHGPQESRA (SEQ ID NO: 17).

The polypeptides of the present invention may generally be prepared using recombinant or synthetic methods that are well known in the art. Recombinant techniques are generally described in Sambrook, et al., Molecular Cloning: A Laboratory Manual, (2nd ed.) Vols. 1–3, Cold Spring Harbor Laboratory, (1989). The term recombinant is also intended to encompass the recombinant expression of heterologous genetic material which is introduced into a host cell or transfectant through viral transfection techniques. Techniques for the synthesis of polypeptides are generally described in Merrifield, J. Amer. Chem. Soc. 85:2149–2456 (1963), Atherton, et al., Solid Phase Peptide Synthesis: A Practical Approach, IRL Press (1989), and Merrifield, Science 232:341–347 (1986). In preferred aspects, the polypeptides of the present invention may be expressed by a suitable host cell that has been transfected with a nucleic acid of the invention, as described in greater detail below.

Biologically active fragments of the above described polypeptides may generally be identified and prepared using methods well known in the art. For example, selective proteolytic digestion, recombinant deletional methods or de novo peptide synthesis methods may be employed to identify portions of the above described peptides that possess the desired biological activity, e.g., AGE binding, presence of immunological determinants, and the like. See, e.g., Sambrook, et al.

Isolation and purification of the polypeptides of the present invention can be carried out by methods that are generally well known in the art. For example, the polypeptides may be purified using readily available chromatographic methods, e.g., ion exchange, hydrophobic interaction, HPLC or affinity chromatography, to achieve the desired purity. Affinity chromatography may be particularly attractive in allowing an individual to take advantage of the specific biological activity of the desired peptide, e.g., AGE binding, presence of antigenic determinants or the like. For example, antibodies raised against human RAGE polypeptides or its immunologically active fragments, may be coupled to a suitable solid support and contacted with a mixture of proteins containing the polypeptides of the invention under conditions conducive to the association of these polypeptides with the antibody. Once bound to the immobilized antibody, the solid support is washed to remove unbound material and/or nonspecifically bound proteins. The desired polypeptides may then be eluted from the solid support in substantially pure form by, e.g., a change in salt, pH or buffer concentration. Alternatively, the affinity of the soluble RAGE polypeptides for AGEs may be used advantageously to purify these peptides. In particular, AGEs, e.g. BSA-AGE, may be immobilized as described above, for use as affinity probes in the purification of the soluble RAGE polypeptides.

In addition to those polypeptides and fragments described above, the present invention also provides fusion proteins which contain these polypeptides or fragments. Fusion proteins may be useful in providing for enhanced expression of the RAGE polypeptide constructs, or in producing RAGE polypeptides having other desirable properties, e.g., labeling groups, e.g., enzymatic reporter groups, binding groups, antibody epitopes, etc.

The term "fusion protein" as used herein, generally refers to a composite protein, i.e., a single contiguous amino acid sequence, made up of two distinct, heterologous polypeptides which are not normally fused together in a single amino acid sequence. Thus, a fusion protein may include a single amino acid sequence that contains two entirely distinct amino acid sequences or two similar or identical polypeptide sequences, provided that these sequences are not normally found together in a single amino acid sequence. Fusion proteins may generally be prepared using either recombinant nucleic acid methods, i.e., as a result of transcription and translation of a gene fusion, which fusion comprises a segment encoding a polypeptide of the invention and a segment encoding a heterologous protein, or by chemical synthesis methods well known in the art.

Also included within the present invention are amino acid variants of the above described polypeptides. These variants may include insertions, deletions and substitutions with other amino acids. For example, in some aspects, conservative amino acid substitutions may be made, i.e., substitution of selected amino acids with different amino acids having similar structural characteristics, e.g., net charge, hydrophobicity and the like. Examples of such conservative substitutions include, e.g., Ala:Val:Leu:Ile:Met, Asp:Glu, Lys:Arg, Asn:Gln, Phe:Tyr and Ser:Thr Glycosylation modifications, either changed, increased amounts or decreased amounts, as well as other sequence modifications are also included within the polypeptides of the invention.

Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch (1992) Ann. Rev. Biochem. 61:387; for example, by adding internal cysteine residues capable of forming intramolecular disulfide bridges which cyclize the peptide. Similarly, modification of the amino or carboxy terminals may also be used to confer stabilizing properties upon the polypeptides of the invention, e.g., amidation of the carboxy-terminus or acylation of the amino-terminus. Substitution of amino acids involved in catalytic activity can be used to generate dominant negative inhibitors of signaling pathways.

Furthermore, although primarily described in terms of "proteins" or "polypeptides" one of skill in the art, upon reading the instant specification, will appreciate that these terms also include structural analogs and derivatives of the above-described polypeptides, e.g., polypeptides having conservative amino acid insertions, deletions or substitutions, peptidomimetics, and the like. For example, in addition to the above described polypeptides which consist only of naturally-occurring amino acids, peptidomimetics of the polypeptides of the present invention are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) Adv. Drug Res. 15:29; Veber and Freidinger (1985) TINS p.392; and Evans et al. (1987) J. Med. Chem. 30:1229, and are usually developed with the aid of computerized molecular modeling. Peptide mimetics that are structurally similar to therapeutically useful peptides may be used to produce an equivalent therapeutic effect. Generally, peptidomimetics are structurally similar to a paradigm polypeptide (i.e., a polypeptide that has a biological or pharmacological activity), such as naturally-occurring receptor polypeptides, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods known in the art and further described in the following references: Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm. Sci. (1980) pp. 463–468 (general review); Hudson, D. et al., Int. J. Pept. Prot. Res. (1979) 14:177–185 (—$CH_2NH$—, $CH_2CH_2$—); Spatola, A. F. et al., Life Sci (1986) 38:1243–1249 (—$CH_2$—S); Hann, M. M., J. Chem. Soc. Perkin Trans. I (1982) 307–314 (—CH—CH—, cis and trans); Almquist, R. G. et al., J. Med. Chem. (1980) 23:1392–1398 (—$COCH_2$—); Jennings-White, C. et al., Tetrahedron Lett. (1982) 23:2533 (—$COCH_2$—); Szelke, M. et al., European Appln. EP 45665 (1982) CA: 97:39405 (1982) (—CH(OH)$CH_2$—); Holladay, M. W. et al., Tetrahedron Lett. (1983) 24:4401–4404 (—C(OH)$CH_2$—); and Hruby, V. J., Life Sci. (1982) 31:189–199 (—$CH_2$—S—).

Peptide mimetics may have significant advantages over polypeptide embodiments, including, for example: more economical production; greater chemical stability; enhanced pharmacological properties (half-life, absorption, potency, efficacy, etc.); altered specificity (e.g., a broad-spectrum of biological activities); reduced antigenicity; and others.

For many applications, it will also be desirable to provide the polypeptides of the invention as labeled entities, i.e., covalently attached or linked to a detectable group, to facilitate identification, detection and quantification of the polypeptide in a given circumstance. These detectable groups may comprise a detectable protein group, e.g., an assayable enzyme or antibody epitope as described above in the discussion of fusion proteins. Alternatively, the detectable group may be selected from a variety of other detectable groups or labels, such as radiolabels (e.g., $^{125}I$, $^{32}P$ or $^{35}S$) or a chemiluminescent or fluorescent group. Similarly, the detectable group may be a substrate, cofactor, inhibitor or affinity ligand. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the molecules to which the peptidomimetic binds (e.g., AGE) to produce the therapeutic effect. Derivitization (e.g., labeling) of peptidomimetics should not substantially interfere with the desired biological or pharmacological activity of the peptidomimetic. Generally, peptidomimetics of peptides of the invention bind to their ligands (e.g., AGEs) with high affinity and/or possess detectable biological activity (i.e., are agonistic or antagonistic to AGE/RAGE interaction and phenotypic changes brought about by those interactions).

III. Antibodies to RAGE

In an additional aspect, the present invention provides antibodies that are specifically immunoreactive with human RAGE and more particularly, the soluble human RAGE polypeptides of the invention. The phrase "specifically immunoreactive," when referring to the interaction between an antibody of the invention and a particular protein, refers to an antibody that specifically recognizes and binds with relatively high affinity to the protein of interest, e.g., RAGE, such that this binding is determinative of the presence of the protein in a heterogeneous population of proteins and other biologics. Thus, under designated immunoassay conditions, the specified antibodies bind to a particular protein and do not bind in a significant amount to other proteins present in the sample. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) Antibodies, A Laboratory Manual, Cold Spring Harbor Publications, New York, for a description of immunoassay formats and conditions that can be used to determine specific immunoreactivity.

For production of polyclonal antibodies, an appropriate target immune system is selected, typically a mouse or rabbit, but also including goats, sheep, cows, guinea pigs, monkeys and rats. The substantially purified antigen is presented to the immune system in a fashion determined by methods appropriate for the animal. These and other parameters are well known to immunologists. Typically, injections are given in the footpads, intramuscularly, intradermally or intraperitoneally. The immunoglobulins produced by the host can be precipitated, isolated and purified by routine methods, including affinity purification.

For monoclonal antibodies, appropriate animals will be selected and the desired immunization protocol followed. After the appropriate period of time, the spleens of these animals are excised and individual spleen cells are fused, typically, to immortalized myeloma cells under appropriate selection conditions. Thereafter, the cells are clonally separated and the supernatants of each clone are tested for the production of an appropriate antibody specific for the desired region of the antigen. Techniques for producing antibodies are well known in the art. See, e.g., Goding et al., Monoclonal Antibodies: Principles and Practice (2d ed.) Acad. Press, N.Y., and Harlow and Lane, Antibodies: A Laboratory Manual, Cold Spring Harbor Laboratory, New York (1988). Other suitable techniques involve the in vitro exposure of lymphocytes to the antigenic polypeptides or alternatively, to selection of libraries of antibodies in phage or similar vectors. Huse et al., Generation of Large Combinatorial Library of the Immunoglobulin Repertoire in Phage Lambda, Science 246:1275–1281 (1989). Monoclonal antibodies with affinities of $10^8$ liters/mole, preferably $10^9$ to $10^{10}$ or stronger, will be produced by these methods.

The antibodies generated can be used for a number of purposes, e.g., as probes in immunoassays, for inhibiting interaction between AGEs and their receptors, in diagnostic or therapeutic applications. These applications are discussed in greater detail, below. Where the antibodies are used to block the interaction between AGEs and their receptors, the antibody will generally be referred to as a "blocking antibody." The antibodies of the present invention can be used with or without modification. Frequently, the antibodies will be labeled by joining, either covalently or non-covalently, a substance which provides for a detectable signal. Such labels include those that are well known in the art, such as the labels described previously for the polypeptides of the invention, e.g., radioactive, fluorescent or bioactive labels. As labeled binding entities, the antibodies of the invention may be particularly useful in, e.g., diagnostic applications, for identifying abnormal levels of RAGE in human tissue or blood samples which abnormal levels may be indicative of the existence of or enhanced potential for those disorders associated with excessive RAGE/AGE interaction, as described herein.

In alternative aspects, the antibodies of the present invention may be used as affinity ligands in the quantitation and/or purification of the RAGE polypeptides from a mixture of proteins. These antibody affinity purification methods are well known in the art, and typically involve the immobilization of a particular antibody, e.g., an antibody to soluble human RAGE, upon a solid support. Solid supports for use in affinity chromatography are generally commercially available from, e.g., Sigma Chemical Co. (St Louis Mo.) and Pharmacia (Uppsala, Sweden).

Additionally, the antibodies of the invention may be chimeric, human-like or humanized, in order to reduce their potential antigenicity, without reducing their affinity for their target. Chimeric, human-like and humanized antibodies have generally been described in the art. Generally, such chimeric, human-like or humanized antibodies comprise hypervariable regions, e.g., complementarity determining regions (CDRs) from a mammalian animal, i.e., a mouse, and a human framework region. See, e.g., Queen, et al., Proc. Nat'l Acad. Sci. USA 86:10029 (1989), Verhoeyan, et al., Science 239:1534–1536 (1988). By incorporating as little foreign sequence as possible in the hybrid antibody, the antigenicity is reduced. Preparation of these hybrid antibodies may be carried out by methods well known in the art.

Preferred antibodies are those monoclonal or polyclonal antibodies which specifically recognize and bind to human RAGE proteins and more particularly, those that specifically bind to the human soluble RAGE polypeptides of the invention. Accordingly, these preferred antibodies will specifically recognize and bind the polypeptides which have an amino acid sequence that is substantially homologous to the amino acid sequence shown in FIG. 1A and 1B (SEQ ID NOS: 1–4), or immunologically active fragments thereof. Still more preferred are antibodies which are capable of forming an antibody-ligand complex with the polypeptides of the invention, whereby the ability of the RAGE polypeptides to associate with their ligands, in vitro, is reduced, e.g., blocking antibodies.

Also preferred are blocking antibodies which inhibit or reduce binding of RAGE to other natural and pathology associated ligands of human RAGE, e.g., amphoterin, β-amyloid peptides, and the like.

IV. Nucleic Acids and Cell Lines

In another aspect, the present invention provides nucleic acids which encode the polypeptides of the invention, as well as expression vectors that include these nucleic acids, and cell lines and organisms that are capable of expressing these nucleic acids. These nucleic acids, expression vectors and cell lines may generally be used to produce the polypeptides of the invention. Generally, the isolated nucleic acids of the present invention encode a polypeptide which is derived from or related to a soluble human RAGE polypeptide or biologically active fragment thereof.

In preferred aspects, the nucleic acid compositions of the invention will typically include a coding region which encodes a polypeptide having an amino acid sequence that is substantially homologous to the amino acid sequence shown in FIG. 1A and 1B (SEQ ID NOS: 1–4). Preferred nucleic acids will typically encode polypeptides having an amino acid sequence which is substantially homologous to the amino acid sequence shown in FIG. 1A and 1B(SEQ ID NOS: 1–4), or biologically active fragments thereof. Such fragments will generally comprise a segment of from about 15 to about 150 nucleotides. These fragments can be useful as oligonucleotide probes in the methods of the present invention, or alternatively to encode the polypeptides or biologically active fragments of the present invention, described herein. Also provided are substantially similar nucleic acid sequences, allelic variations and natural or induced sequences of the above described nucleic acids. Also included are chemically modified and substituted nucleic acids, e.g., those which incorporate modified nucleotide bases or which incorporate a labelling group.

More preferred nucleic acids will comprise a segment having more than about 20 contiguous nucleotides from the nucleotide sequences shown in either of FIG. 1A or 1B (SEQ ID NOS: 1–4), with still more preferred nucleic acids having a nucleotide sequence that is substantially homologous to either of the nucleotide sequences shown in FIG. 1A or 1B(SEQ ID NOS: 1–4). Most preferred nucleic acids are those which include a portion, i.e., at least 20 contiguous nucleotides, or all of the nucleotide sequence shown in FIGS. 1A or B(SEQ ID NOS: 1–4).

"Nucleic acids" of the present invention include RNA, cDNA, genomic DNA, synthetic forms and mixed polymers, both sense and antisense strands. Furthermore, different alleles of each isoform are also included. The present invention also provides recombinant nucleic acids which are not otherwise naturally occurring. The nucleic acids described herein also include self replicating plasmids and infectious polymers of DNA or RNA. Unless specified otherwise, conventional notation for nucleic acids is used herein. For example, as written, the left hand end of a single stranded polynucleotide sequence is the 5'-end, whereas the right-hand end is the 3'-end. The left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It will be further understood that the nucleic acids of the invention also encompass degenerate codons of the native sequence or sequences which may be introduced to provide codon preference in a specific host cell.

Substantial homology in the nucleic acid context means that the segments, or their complementary strands, when compared, are the same when properly aligned, with the appropriate nucleotide insertions or deletions, in at least about 60% of the nucleotides, typically, at least about 70%, more typically, at least about 80%, usually, at least about 90%, and more usually, at least about 95% to 98% of the nucleotides. Alternatively, substantial homology exists when the segments will hybridize under selective hybridization conditions to a strand, or its complement, typically using a sequence of at least about 20 contiguous nucleotides derived from the nucleotide sequences shown in FIGS. 1A or 1B (SEQ ID NOS: 1–4). However, larger segments will usually be preferred, e.g., at least about 30 contiguous nucleotides, more usually about 40 contiguous nucleotides, and preferably more than about 50 contiguous nucleotides. Selective hybridization exists when hybridization occurs which is more selective than total lack of specificity. See, Kanehisa, Nucleic Acid Res. 12:203–213 (1984). Examples of such selective hybridization conditions include, e.g., hybridization under the hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

The nucleic acids of the present invention may be present in whole cells, cell lysates or in partially pure or substantially pure or isolated form. When referring to nucleic acids, the terms "substantially pure" or "isolated" generally refer to the nucleic acid separated from contaminants with which it is generally associated, e.g., lipids, proteins and other nucleic acids. The substantially pure or isolated nucleic acids of the present invention will be greater than about 50% pure. Typically, these nucleic acids will be more than about 60% pure, more typically, from about 75% to about 90% pure and preferably from about 95% to about 98% pure.

There are various methods of isolating the nucleic acids which encode the polypeptides of the present invention. Typically, the DNA is isolated from a genomic or cDNA library using labeled oligonucleotide probes specific for sequences in the desired DNA. Restriction endonuclease digestion of genomic DNA or cDNA containing the appropriate genes can be used to isolate the DNA encoding the polypeptides of the invention. From the nucleotide sequence given in FIGS. 1A or 1B(SEQ ID NOS: 1–4), a panel of restriction endonucleases can be constructed to give cleavage of the DNA in desired regions, i.e., to obtain segments which encode biologically active polypeptides or fragments of the invention. Following restriction endonuclease digestion, DNA encoding the polypeptides of the invention is identified by its ability to hybridize with a nucleic acid probe in, for example, a Southern blot format. These regions are then isolated using standard methods. See, e.g., Sambrook, et al., supra.

The polymerase chain reaction, or "PCR" can also be used to prepare nucleic acids which encode the polypeptides of the present invention. PCR technology is used to amplify nucleic acid sequences of the desired nucleic acid, e.g., the DNA which encodes the polypeptides of the invention, directly from mRNA, cDNA, or genomic or cDNA libraries.

Alternatively, solid phase oligonucleotide synthesis methods may also be employed to produce the nucleic acids described herein. Such methods include the phosphoramidite method described by, e.g., Beaucage and Carruthers, Tetrahedron Lett. 22:1859–1862 (1981), or the triester method according to Matteucci, et al., J. Am. Chem. Soc., 103:3185 (1981). A double stranded fragment may then be obtained, if desired, by annealing the chemically synthesized single strands together under appropriate conditions or by synthesizing the complementary strand using DNA polymerase with an appropriate primer sequence.

Appropriate primers and probes for amplifying the nucleic acids described herein, may be generated from analysis of the nucleic acid sequences described herein, e.g., in FIG. 1A or 1B(SEQ ID NOS: 1–4). Briefly, oligonucleotide primers complementary to the two 3' borders of the DNA region to be amplified are synthesized. The PCR is then carried out using the two primers. See, e.g., PCR Protocols: A Guide to Methods and Applications (Innis, M., Gelfand, D., Sninsky, J. and White, T., eds.) Academic Press (1990). Primers can be selected to amplify a variety of different sized segments from the nucleic acid sequence.

In addition to their use in producing the polypeptides of the invention, the nucleic acid sequences described herein are also particularly useful in a number of other applications. For example, in a particular aspect, the nucleic acid sequences of the present invention or fragments thereof, may be readily employed as nucleic acid probes useful in obtaining genes which encode the polypeptides of the present invention or other closely related genes. "Nucleic acid probes" may be DNA or RNA fragments. DNA fragments can be prepared, for example, by digesting plasmid DNA, or by use of PCR, or synthesized by either the phosphoramidite or phosphotriester methods described in, e.g., Gait, Oligonucleotide Synthesis: A Practical Approach, IRL Press (1990). Where a specific sequence for a nucleic acid probe is given, it is understood that the complementary strand is also identified and included. The complementary strand will work equally well in situations where the target is a double-stranded nucleic acid. Typical nucleic acid probes may be readily derived from the nucleotide sequence shown in FIG. 1A or B(SEQ ID NOS: 1–4), or alternatively, may be prepared from the amino acid sequence of soluble human RAGE polypeptides, as shown in FIG. 1A or 1B(SEQ ID NOS: 1–4). In particular, probes may be prepared based upon segments of the amino acid sequence which possess relatively low levels of degeneracy, i.e., few or one possible nucleic acid sequences which encode therefor. Suitable synthetic DNA fragments may then be prepared.

Such nucleic acid probes, e.g., cDNA probes, may be used in the design of oligonucleotide probes and primers for screening and cloning genes which encode the polypeptides of the invention or related polypeptides, e.g., using well known PCR techniques. These nucleic acids, or fragments may comprise part or all of the cDNA sequence that encodes the polypeptides of the present invention. Effective cDNA probes may comprise as few as 15 consecutive nucleotides in the cDNA sequence, but will often comprise longer segments. Further, these probes may further comprise an additional nucleotide sequence, such as a transcriptional primer sequence for cloning, or a detectable group for easy identification and location of complementary sequences. Examples of probes that are particularly useful in amplifying the nucleic acid sequence encoding soluble human RAGE as shown in FIG. 1A or 1B, include those having the following sequences: 5'-GATGGCAGCCGGAACAGCAGTT-3'(SEQ ID NO: 22); and 5'-CTCAAGTTCCCAGCCCTGAT CCTCC-3'(SEQ ID NO: 23).

cDNA or genomic libraries of various types may be screened for new alleles encoding RAGE or related sequences, using the above probes. The choice of cDNA libraries normally corresponds to tissue sources which are abundant in mRNA for the desired polypeptides, e.g., lung tissue. Phage or plasmid libraries may generally be used. Clones of a library are spread onto plates, transferred to a substrate for screening, denatured, and probed for the presence of the desired sequences.

In addition to comprising a segment which encodes one or more of the above described polypeptides or biologically active fragments, the nucleic acids of the present invention may also comprise a segment encoding a heterologous protein, such that the gene is expressed to produce the two proteins as a fusion protein, as substantially described above.

Typically, the nucleic acids of the present invention will be used in expression vectors for the preparation of the polypeptides of the present invention, namely those polypeptides which are derived from or related to soluble human RAGE or its biologically active fragments. The phrase "expression vector" generally refers to nucleotide sequences that are capable of affecting expression of a structural gene in hosts compatible with such sequences. These expression vectors typically include at least suitable promoter sequences and optionally, transcription termination signals. Additional factors necessary or helpful in effecting expression may also be used as described herein. DNA encoding the RAGE polypeptides of the present invention will typically be incorporated into DNA constructs capable of introduction into and expression in an in vitro cell culture. Often, the nucleic acids of the present invention may be used to produce a suitable recombinant host cell. Specifically, DNA constructs will be suitable for replication in a prokaryotic host, such as bacteria, e.g., *E. coli*, or may be introduced into a cultured mammalian, plant, insect, e.g., Sf9, yeast, fungi or other eukaryotic cell line. DNA constructs prepared for introduction into a particular host, e.g., insect or bacteria, will typically include a replication system recognized by the host, the intended DNA segment encoding the desired polypeptide, and transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See, e.g., Sambrook et al., Molecular Cloning: A Laboratory Manual (2d ed.), vols. 1–3 Cold Spring Harbor Laboratory (1989). The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al., (1989).

Conveniently available expression vectors which include the replication system and transcriptional and translational regulatory sequences together with the insertion site for the polypeptide encoding segment may be employed. Examples of workable combinations of cell lines and expression vectors are described in Sambrook et al., and in Metzger et al., Nature 334:31–36 (1988). For example, suitable expression vectors may be expressed in, e.g., insect cells, e.g., Sf9 cells, mammalian cells, e.g., CHO cells and bacterial cells, e.g., *E. coli*.

Where an insect cell line is selected as the host cell of choice to express the polypeptide, the cDNA encoding the polypeptides of the invention may be cloned into an appropriate baculovirus expression vector, e.g., pBacPAK8 vector (Clontech, Palo Alto, Calif.). The recombinant baculovirus may then be used to transfect a suitable insect host cell, e.g., Spodoptera frugiperda (Sf9) cells, which may then express the polypeptide. See, e.g., D. K. Morrison et al., Cell 58:649–657 (1989), M. D. Summers and G. E. Smith, A Manual of Methods for Baculovirus Vectors and Insect Cell Culture Procedures, Texas Agricultural Station, College Station, Tex. (1987).

V. Methods of Use

The compositions of the present invention have a wide variety of uses, including, inter alia, screening, diagnostic and therapeutic applications.

A. Screening Applications

In a preferred aspect, the polypeptides of the invention may be used as model systems for identifying effectors of the AGE/RAGE interaction. In particular, these model systems may be used to screen collections or libraries of test compounds in order to identify agonists or antagonists of AGE/RAGE interaction. Generally, agonists, antagonists or test compounds may be chemical compounds, mixtures of chemical compounds, biological macromolecules, or extracts made from biological materials such as bacteria, plants, fungi, or animal cells or tissues. Particularly targeted test compounds will typically include the polypeptides or fragments of the present invention as well as structural analogs or peptidomimetics which are derived from these polypeptides or the antibodies described herein, substrates or ligands thereof. As used herein, the term "agonist" refers to a composition or compound that will enhance the particular observed activity, e.g., AGE/RAGE binding, while an "antagonist" will diminish the particular observed activity. The terms "agonist" and "antagonist", as used herein, do not imply any particular mechanism of function.

The screening methods of the present invention typically involve the incubation of a polypeptide of the present invention, e.g., a soluble human RAGE polypeptide, in the presence of a standard advanced glycosylation end-product protein (AGE) such as AGE-BSA, nonenzymatically N-glycosylated collagen, myelin or the like, as well as the test compound. Typically, one of the RAGE polypeptide or AGE will be immobilized upon a solid support which will then be contacted with the other protein or peptide. The other, non-immobilized member of the AGE/RAGE pair will typically include a labeling group covalently or otherwise attached so as not to interfere with the AGE/RAGE interaction. Labeling groups will generally include those that are substantially set out above. Immobilization of one of the AGE or RAGE polypeptide permits ready separation of AGE/RAGE complex, which will be bound to the solid support, from unreacted or free AGE or RAGE, utilizing a simple wash step.

A number of suitable solid supports may be employed for immobilization of the AGE or RAGE polypeptides. Examples of suitable solid supports include agarose, cellulose, dextran, Sephadex, Sepharose, carboxymethyl cellulose, polystyrene, filter paper, nitrocellulose, ion exchange resins, plastic films, glass beads, polyaminemethylvinylether maleic acid copolymer, amino acid copolymer, ethylene-maleic acid copolymer, nylon, silk, etc. The support may be in the form of, e.g., a test tube, microtiter plate, beads, test strips, or the like. The reaction of the AGE or RAGE polypeptide with the particular solid support may be carried out by methods well known in the art. For example, in some cases, supports bearing lectins, e.g., Con-A, may be employed for immobilization of the AGEs. Alternatively, a variety of pre-derivatized solid supports to which AGEs may be covalently attached are generally available from, e.g., Sigma Chemical Co. (St. Louis, Mo.), and Pharmacia (Upsalla, Sweden).

In the case of a microtiter plate, the test compound may be added to the well of the microtiter plate to preincubate with the immobilized AGE or RAGE polypeptide. The remaining member of the RAGE/AGE pair, bearing a suitable labeling group as described previously, may then be added to the microtiter well. Following suitable incubation, the wells are washed, and the amount of bound label is determined, e.g., by scanning the plate with a suitable optical reader, e.g., plate reader. The level of binding is then compared to suitable positive and negative controls or a set of standards containing a known range of agonists or antagonist concentrations. Alternatively, by providing the polypeptide containing the RAGE and AGE polypeptides in known concentrations, one can assay for the level of free or unbound RAGE or AGE, and by negative implication, determine the level of RAGE/AGE complex which is formed.

In some cases, identification of complexed AGE/RAGE may be carried out by other means, i.e., without the use of a support bound peptide. For example, well known quantitation methods, such as HPLC and the like may be utilized to separate and identify complexed AGE/RAGE polypeptides from the free or uncomplexed proteins. Again, this may allow determination and comparison of the amount of either the free or bound material remaining after incubation with the test compound.

Where the presence of the test compound results in a decrease of the amount of RAGE/AGE complex formed, it will be indicative that the test compound is an antagonist of the RAGE/AGE interaction. Where, however, the presence of a test compound results in an increase or enhancement of RAGE/AGE interaction, it will be indicative that the compound is an agonist of the RAGE/AGE interaction. Test compounds which are indicated to be antagonists of the RAGE/AGE interaction may be further characterized in additional studies, e.g., clinical trials.

B. Affinity Ligands

In addition to their use as screening systems, the peptides of the invention may also be used as affinity ligands which specifically bind to AGEs. As affinity ligands, these polypeptides may also be useful in the purification of AGEs from a mixture of different proteins. Affinity purification of AGEs may be carried out using affinity purification methods that well known in the art. For example, the soluble RAGE polypeptide or peptides may be attached to a suitable solid support as described above. Many solid supports are commercially available from, e.g., Sigma Chemical Co., St Louis, Mo., or Pharmacia, Uppsala, Sweden, and come prepared for immediate coupling of affinity ligands.

The mixture of proteins may be contacted with the polypeptide bound to the solid support, such that the RAGE polypeptide immobilized upon the solid support can selectively bind the AGEs within the mixture of proteins. The bound protein can then be washed to eliminate unbound proteins. Finally, substantially pure AGEs may be eluted from the solid support by generally known elution protocols, e.g., changing buffer conditions, temperature, or level of carbohydrate in the elution buffer.

As affinity probes, the polypeptides of the invention may also be used to bind AGEs both in vitro and in vivo. This binding may be used in assay formats to label and detect AGEs in a sample, imaging formats to identify localization of AGEs in a patient, or in therapeutic applications to deliver a drug to areas which are relatively high in AGE concentration, or specifically deliver a drug, e.g., a proteolytic drug, to an AGE.

In a similar manner, the antibodies of the invention may also be used as affinity probes or ligands for soluble RAGE polypeptides. In particular, the specificity of the antibodies of the invention may be exploited in the purification and/or identification of RAGE polypeptides and particularly, soluble human RAGE polypeptides.

C. Diagnostic Applications

As alluded to above, the polypeptides of the invention may be used as probes capable of specifically interacting with their ligands, i.e., AGEs. As a result, the polypeptides of the invention may be used in a variety of diagnostic applications. For example, those polypeptides of the invention that are capable of specifically interacting with AGEs may be particularly useful in identifying patients who may suffer from abnormal levels of AGEs which are indicative of particular disorders, or may be viewed as indicators of future problems, such as diabetic vasculopathy.

In a particular aspect, soluble human RAGE polypeptides may be used as affinity probes to identify the presence, absence and/or relative quantity of AGEs in a sample, e.g., blood or tissue samples from a patient. This allows the identification of patients having elevated levels of AGE or other ligands of RAGE, which levels are indicative of a variety of pathological conditions associated with, e.g., Diabetes Mellitus, peripheral occlusive vascular diseases, hemodialysis-associated amyloidosis, Alzheimer's disease and other age-related disorders. Once a patient is diagnosed as suffering from one or more of these complications, or is identified as being at a higher risk, appropriate preventative or therapeutic measures may be taken, such as administration of appropriate pharmaceutical agents, e.g., compositions comprising the peptides, peptidomimetics or antibodies of the invention.

In a similar manner, the antibodies of the present invention, e.g., those that are specifically immunoreactive with human RAGE polypeptides, may be used to diagnose disorders characterized by abnormal levels or localization of AGE/RAGE interactions. In particular, the described antibodies may be used as diagnostic tools to evaluate plasma and tissue levels of RAGE in patients suffering from pathological conditions associated with elevated levels of AGE/RAGE interaction. In particular, the antibodies described herein may be used in well known immunoassay formats, e.g., ELISA, Western blotting, immunohistochemistry and FACS methods, to identify levels of RAGE in samples.

D. Therapeutic Applications

In addition to the above described uses, the soluble RAGE polypeptides and antibodies of the invention may also be used in therapeutic applications for the treatment of human or non-human mammalian patients. The term "treatment" as used herein, refers to the full spectrum of treatments for a given disorder from which the patient is suffering, including alleviation of one, most or all symptoms resulting from that disorder, to an outright cure for the particular disorder or prevention of the onset of the disorder.

In particular, the polypeptides and antibodies of the invention are useful in treating disorders or symptoms of which result from excessive levels of AGEs in tissue or plasma. As described previously, the association of AGEs and RAGE has been implicated as a symptom or causative event in a number of pathological conditions including, e.g., complications associated with Diabetes Mellitus, e.g., diabetic microvasculopathy (neuropathy, nephropathy and retinopathy), diabetic macrovasculopathy (atherosclerosis), occlusive vascular disorders, activation of microglial cells by β-amyloid peptides in Alzheimer's disease, hemodialysis-associated amyloidosis and age related disorders such as oxidant stress. Accordingly, treatment or prevention of such disorders may generally be carried out by reducing, inhibiting or outright blocking the interaction between AGEs and RAGE. Blocking this interaction typically involves administering to a patient an effective amount of a soluble human RAGE polypeptide, peptidomimetc or blocking antibody, as described above.

The term "patient" generally refers to a mammalian individual, typically human, who has been diagnosed as suffering from one or more of the above described disorders, or who has been characterized as belonging to a group that has an abnormally high incidence of such disorders, e.g., diabetics and the elderly.

The term "effective amount" or "therapeutically effective amount" generally refers to the quantities of reagents necessary for effective therapy, i.e., the partial or complete alleviation of the symptom or disorder for which treatment was sought. Included within the definition of effective therapy are preventative treatments intended to reduce the likelihood of onset of the above-described symptoms or disorders. The effective amount for a given therapy, whether curative or preventative, will generally depend upon many different factors, including means of administration, target site, physiological state of the patient and other medicants administered. Thus, treatment doses will need to be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Generally, therapeutically effective amounts of the polypeptides or blocking antibodies of the present invention will be from about 0.0001 to about 10 mg/kg, and more usually, from about 0.001 to about 0.1 mg/kg of the host's body weight. Various considerations are described, e.g., in Gilman et al., (Eds.), Goodman and Gilman's: The Pharmacological Basis of Therapeutics, (8th ed. 1990), Pergamon Press, and Remington's Pharmaceutical Sciences (7th ed. 1985) Mack Publishing Co., Easton, Pa.

Methods of administration, also discussed in the above references, include, e.g., oral, intravenous, intraperitoneal or intramuscular administration, and local administration, including topical, transdermal diffusion and aerosol administration, for therapeutic, and/or prophylactic treatment. The active agent, i.e., the polypeptide or antibody component, will generally be administered in a composition additionally comprising a pharmaceutically acceptable carrier. Suitable pharmaceutically acceptable carriers include water, saline, buffers and other compounds described in, e.g., the Merck Index, Merck and Co., Rahway, N.J. For some methods of administration, e.g., oral, it may be desirable to provide the active ingredient in a liposomal formulation. This is particularly desirable where the active ingredient may be subject to degradative environments, for example, proteolytic digestive enzymes. Liposomal formulations are well known in the art, and are discussed in, e.g., Remington's Pharmaceutical Sciences, supra. Administration may also be carried out by way of a controlled release composition or device, whereby a slow release of the active ingredient allows continuous administration over a longer period of time.

Constituents of pharmaceutical compositions, in addition to the active agents described herein, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline and the like. Additionally, these compositions may include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

Administration may also be carried out by way of a controlled release composition or device, whereby a slow release of the active ingredient allows continuous administration over a longer period of time.

The present invention is further illustrated by the following examples. These examples are merely to illustrate aspects of the present invention and are not intended as limitations of this invention.

VI. Examples

EXAMPLE 1:

Cloning, Expression and Purification of Soluble Human RAGE

A DNA fragment coding for human soluble RAGE was obtained from lung cDNA library using polymerase chain reaction techniques (PCR, GeneAmp, Perlin-Elmer Cetus); primers used were 5'-GATGGCAGCCGG AACAGCAGTT-3' (SEQ ID NO: 22) and 5'-CTCAAGTTCCCAGCCCTG ATCCTCC-3'(SEQ ID NO: 23). The DNA sequence of the PCR product was confirmed by the dideoxy chain termination method (Sanger, et al., Proc. Nat'l Acad. Sci. USA 74:5463–5467 (1977). The DNA fragment was subcloned into the pCRII™ vector (Invitrogen, San Diego, Calif.) and the EcoR1 fragment of the resulting plasmid was cloned into the pBacPAK8 vector (Clontech, Palo Alto, Calif.) under control of the AcMNPV polyhedrin promoter (ATCC Accession Nos. VR-2538 and VR-2539) Both deposits were made on Jul. 10, 1996, at the American Type Culture Collection (ATCC), 10801 University Boulevard, Manassas, Va. 20112-2209. Baculovirus expression of recombinant human soluble RAGE was performed by co-transfecting the plasmid pBacPAK8/RAGE with a linearized BacPAK6 viral cDNA (Clontech) into *Spodoptera frugiperda* (Sf9) cells according to the manufacturer's instructions. Recombinant plaques were identified and purified by their beta-galactosidase negative phenotype.

Sf9 cells expressing soluble RAGE were grown as follows: Non-infected Sf 9 cells were grown in shake flasks at 28° C., to a density of 1–1.2 ×10$^6$/ml in TNMF (Grace's with supplements from Sigma) plus 10% FBS (e.g. Hyclone) and 0.1% pluronic F-68 (Sigma), and a viability of >97%. One liter of cells was infected with viral stock (MOI of ~0.01). Cultures were harvested 3 days post-infection by centrifuging the media at 1200 rpm for 8 min. This media was then used for purification of recombinant soluble RAGE.

Recombinant human soluble RAGE was purified from the Sf9 media by chromatography on an SP Sepharose fast flow column (Pharmacia) followed by a size exclusion chromatography step. In particular, a 1/10 volume of 1.0 M Tris-HCl, pH 8.0 was added to Sf 9 cell media to precipitate viral proteins and the media was allowed to sit at 4° C. for several hours to allow precipitation. The precipitated media was centrifuged at ~3000 rpm for 10 to 15 min to remove any precipitate. The supernatant was diluted 1:4 with deionized water, adjusted to pH 7.5 and sterile filtered (0.2 μm). The filtered supernatant was loaded onto SP Sepharose fast flow column (#17-0729-01, Pharmacia), that had been equilibrated with 20 mM NaP04, pH 7.5. The column was eluted in a salt gradient from 0 to 0.5 M NaCl, and the fractions were analyzed by SDSPAGE. Fractions containing RAGE were pooled, concentrated and diafiltered into PBS buffer.

Further purification was obtained by applying the pooled fractions to a Superdex 200 PG column, and again, fractions were analyzed by SDS-PAGE and pooled as appropriate.

EXAMPLE 2:

Solid Phase Binding Assays for Soluble Human RAGE

Two assay formats were used to assess the ability of soluble RAGE to bind AGE. The first provided a RAGE polypeptide immobilized directly to the solid support whereas the second method employed an indirect attachment to more closely mimic the cell surface presentation of the AGE binding portion of RAGE.

A. Preparation of AGE-BSA and $^{125}$I-AGE-BSA

Bovine serum albumin (from Sigma, Cat #A7888) was incubated at a concentration of 25 mg/ml in phosphate buffered saline (calcium- and magnesium-free) with 250 mM ribose, in the presence of 1.5 mM PMSF (phenylmethylsulfonyl fluoride) and 1 mM EDTA (ethylenediaminetetraacetic acid). The pH of the solution was adjusted to between 6.8 and 7.0. The solution was sterilized by filtering through 0.22 micron filters and incubated in dark, at 37° C. for 6 to 8 weeks. The solution containing AGE-BSA was dialysed against calcium- and magnesium-free PBS, and stored frozen in aliquots at −20° C.

100 μg of AGE-BSA was iodinated with 1 mCi of Na$^{125}$I using iodogen method according to the manufacturer's specifications. 4 μl of AGE-BSA (100 μg), 8 μl of Na$^{125}$I (1 mCi) and 88 μl of phosphate buffered saline was added to a tube containing iodo-gen (Pierce). The tube was incubated for 15 minutes on ice, with occasional agitation. The reaction was terminated by adding 50 μl of 0.1% potassium iodide. The reaction mixture was passed over a desalting column to remove free iodine.

B. Competitive Binding of AGE to Indirectly Immobilized RAGE

Figure 2B:
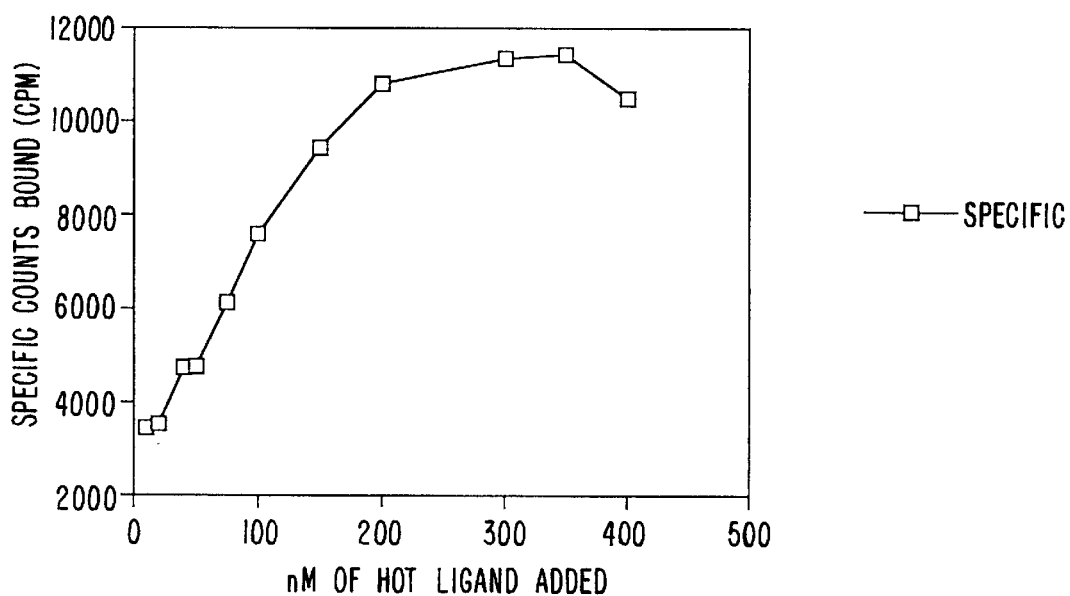

A 96-well plate (Immunolon 4 from Dynatech Lab) was coated with anti-flag peptide antibodies (Eastman Kodak), 100 μl/well of 17 μl/ml in sodium bicarbonate buffer, pH 9.6) at 4° C. overnight. The wells were washed and blocked as above. The wells were then incubated with Sf 9 media containing human recombinant soluble RAGE/flag fusion protein (75 μl of 1:4 dilution with PBS) 1 to 2 h at 37° C. (flag peptide: DYKDDDDK). The wells were again washed as before and incubated with various concentrations of $^{125}$I-AGE-BSA alone or in the presence of excess cold AGE-BSA (i.e., nonradioactive) in PBS containing 0.2% BSA (45 μl/well) at room temperature for 23 hours. The sample having an excess of cold AGE-BSA was used to account for nonspecific interactions. The wells were washed twice with 0.2% BSA in PBS. The bound ligand was then eluted with PBS containing 1 mg/ml of heparin and 1 mg/ml of BSA (100 μl/well) by incubating at 37° C. for 5 minutes and counted. FIG. 2 shows a graph of AGE binding to indirectly immobilized RAGE (expressed as CPM) as a function of increasing ligand concentration, in the absence and presence of excess nonradioactive ligand (FIG. 2A), and corrected for nonspecific interactions (FIG. 2B).

EXAMPLE 3:

Competition Binding Assays Using Soluble Human RAGE

Competition assays were also performed between $^{125}$I-AGE-BSA and an excess of a number of other proteins, including soluble RAGE, Soluble RAGE/flag fusion protein, recombinant soluble RAGE/DCC chimeric protein (where the first Ig-like domain of RAGE is substituted with the first Ig-like domain of DCC, another Ig-superfamily member), lactoferrin and native BSA. The results are shown in Table 1, below.

TABLE 1

| Results of Competition Binding Assay (% Binding) | | | |
|---|---|---|---|
| | Exp. 1 | Exp. 2 | Exp. 3 |
| $^{125}$I-AGE-BSA only | 100% | 100% | 100% |
| + cold AGE-BSA | 29% | 14% | 12% |
| + rec. solRAGE | n.d. | 65% | 60% |
| + rec. solRAGE/flag fusion | 8% | n.d. | n.d. |
| + rec. solRAGE/DCC chimeric | 40% | n.d. | n.d. |
| + lactoferrin | n.d. | 50% | 20% |
| + native BSA | n.d. | >100% | >100% | n.d.- Not determined

Figure 3:
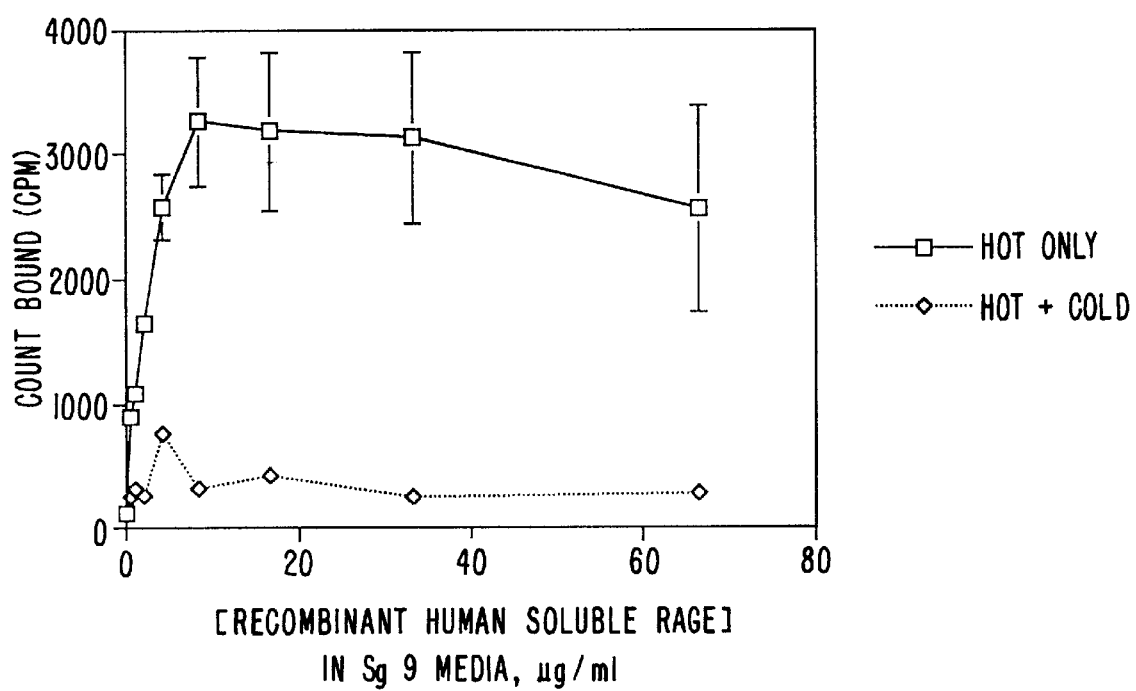
FIG. 3 shows a dose response curve for RAGE/AGE binding in the presence of increasing concentrations of free RAGE

Binding assays were done in quadruplicate. Lactoferrin has been previously shown to bind AGEs. Li et al. Nature med. 1(10):1057–1061 (1995). Furthermore, lactoferrin was also shown to bind to RAGE Schmidt et al., J. Biol. Chem. 269:9882–9888 (1994), Yan et al., J. Biol. Chem. 269:9889–9897 (1994). However, as is apparent from the Table 1, binding of lactoferrin to RAGE or AGE does not facilitate further binding of AGE-BSA to RAGE. FIG. 3 is dose response curve for the formation of RAGE/AGE binding complex in the presence of increasing concentrations of soluble RAGE polypeptide. As shown, increasing concentration of soluble RAGE increased the levels of AGE/RAGE binding until a plateau was reached.

EXAMPLE 4:

Preparation of Antibodies to Human Soluble RAGE

Monoclonal antibodies were generated from mice immunized with the human soluble RAGE extracellular domain expressed in baculovirus as described above.

Hybridoma preparation: Pairs of mice from three strains (Balb/C, Swiss Webster, and RBF/DnJ) were immunized with 100 μg soluble RAGE in complete Hunter's adjuvant, intradermally, on days 0, 7, and 21. Sera were drawn on day 28, and titers tested by EIA of soluble RAGE and FACS analysis of CHO-RAGE transfectants. Two mice were selected as lymphocyte donors, and received 5 μg soluble RAGE IV 72 hours before fusion. Splenocytes from these mice were fused with the mouse myeloma P3X63Ag8.653, and the resultant fusion products were selected with hypoxanthine-aminopterin-thymidine (HAT). Following HAT selection, supernatants from 2100 clones were tested in direct EIA with soluble RAGE. Seventy two strongly positive clones were isolated and then tested for reactivity to CHO RAGE transfectant cells, of which 69 clones were positive. Selected hybridomas were serially subcloned 3 X by limiting dilution, and ascites induced in pristane primed IRCF1 mice. The antibodies were purified by affinity chromatography (Protein G) followed by ion exchange chromatography (Q-Sepharose). Purity was tested by reduced SDS-PAGE, and isotype analysis was done by radial immunodiffusion.

The resultant panel was tested for reactivity by EIA, Western blot, and FACS analysis of CHO cells transfected with full length RAGE. The antibodies were also analyzed for epitope variance by competition, and reactivity with RAGE/DCC chimeric protein. Complementary pairs of antibodies were selected, and antigen capture EIAs specific for human, rat, and mouse RAGE were designed, with sensitivity in the nanogram range.

EIA: Direct antibody capture EIA was done by coating 96-well microtiter plates with 1 μg/well antigen in PBS, and incubating overnight at 4 C. Wells were blocked with PBS/1% BSA or casein, anti-RAGE antibodies added as either neat tissue culture supernatant or 1 μg/well diluted in PBS/1% BSA and incubated for 2 hours at ambient room temperature. After washing 3 X with PBS, anti-mouse IgG-alkaline phosphatase was added, and substrate degradation analyzed at 405 nm with a UVMax plate reader.

Antigen capture (sandwich) EIAs were done as above, with the additional step of coating wells with 2 μg anti-RAGE monoclonal antibody diluted in carbonate buffer, pH 9.6, before addition of antigen.

Western Blot: Cell culture supernatants containing human, rat, or mouse RAGE were harvested, and size fractionated on denaturing SDS-PAGE gels. The proteins were transferred to nitrocellulose, incubated with anti-RAGE antibody, and developed using an Amersham detection kit.

FACS analysis: Cells (CHO-RAGE, parental CHO, mouse macrophage, and human smooth muscle aorta) were harvested, and incubated with 5 μg per 106 cells anti-RAGE antibody for 45 minutes on ice. After washing with cold PBS, cells were then incubated with anti-mouse IgG-FITC or phycoerythrin for 45 minutes on ice and then washed with PBS. Cells were analyzed for mean channel fluorescence with a Becton-Dickinson FACScan.

Ligand binding analyses and antibody competition studies were done as above, with additional incubations with lactoferrin, and double labelled detection with anti-lactoferrin antibody in parallel with the anti-RAGE antibody.

Figure 4A:
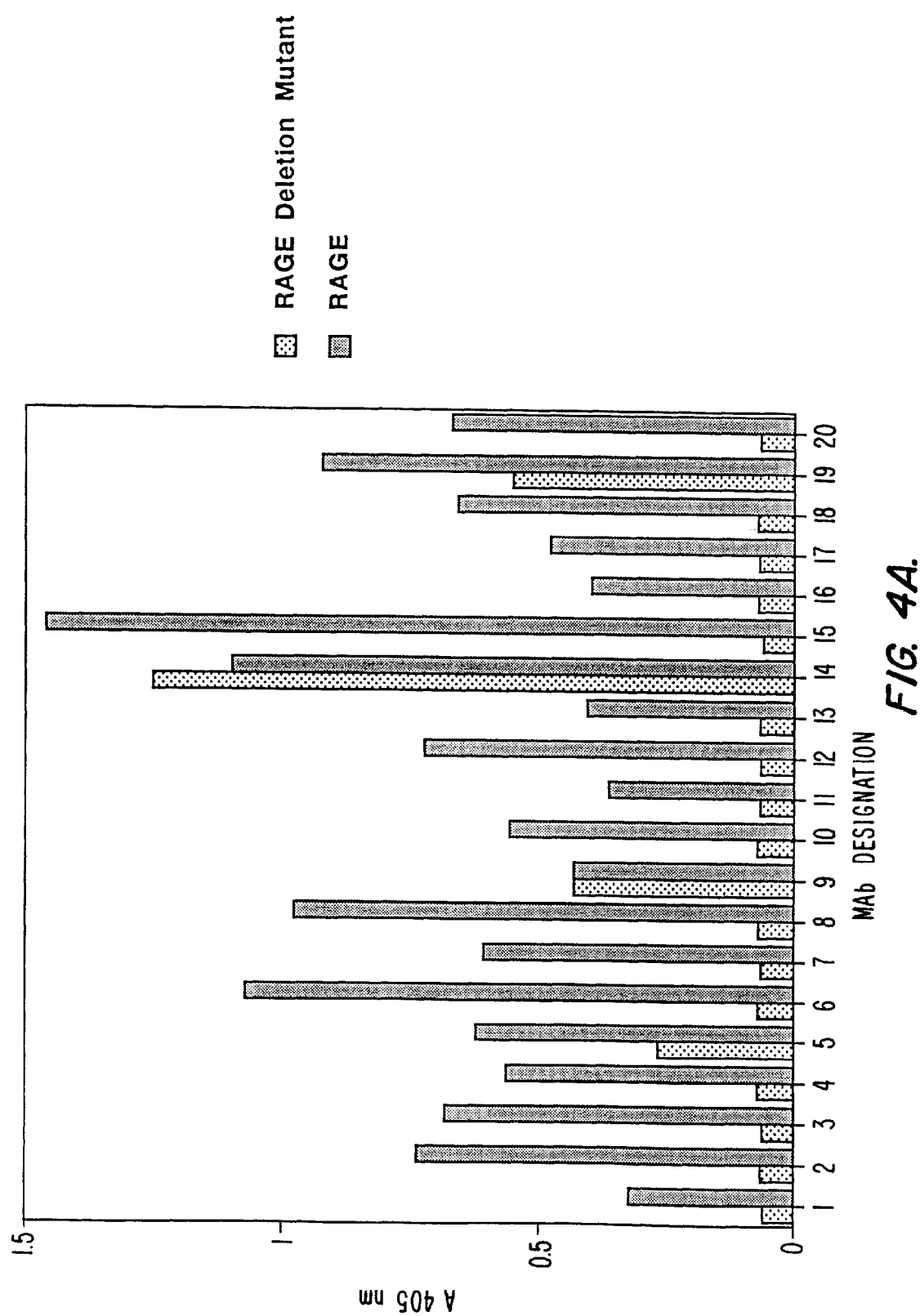
FIG. 4A is a bar graph showing levels of antibody binding to human soluble RAGE using an EIA antibody capture assay. Binding is compared between intact soluble RAGE (dark bars) and RAGE/DCC chimeric protein (in which the first Ig-like domain of RAGE is replaced with the first Ig-like domain of DCC, a member of the Ig superfamily. Four antibodies (#5, 9, 14 and 19) recognized both the intact soluble RAGE and the chimeric protein.

The direct antibody capture EIA was used as the initial fusion screen to identify positive clones. The assay format was also utilized to determine reactivity with the RAGE chimeric RAGE/DCC protein in which the first immunoglobulin-like domain was replaced with that of DCC. The assay results for the first 20 MAbs are shown in FIG. 4. Four MAbs recognized both intact soluble RAGE polypeptide as well as the chimeric protein indicating epitope location outside the first Ig-like domain.

Figure 4B:
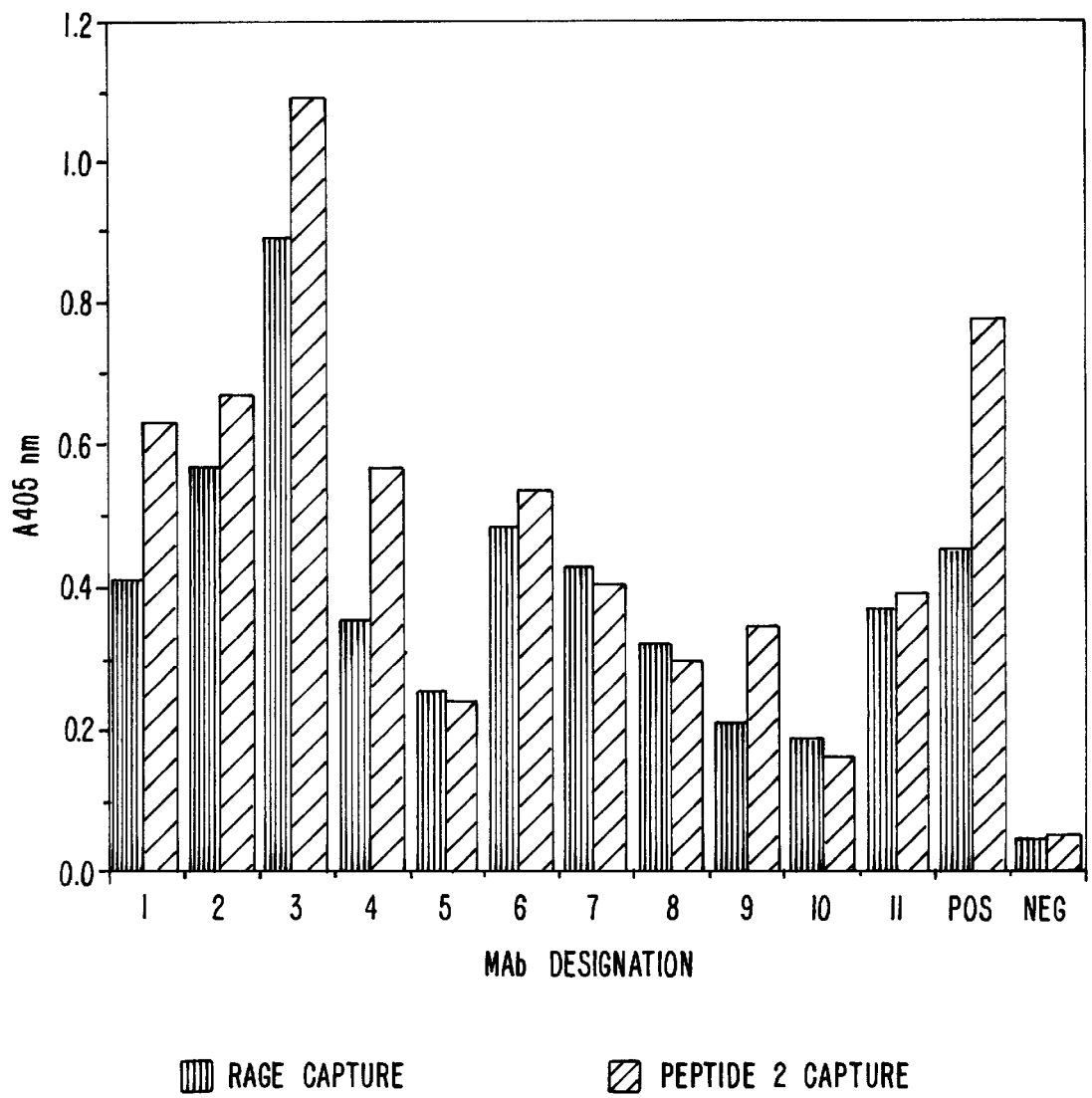
FIGS. 4B and 4C show antibody binding to peptide fragments of soluble human RAGE, designated peptide 1 (CKGAPKKPPQ) (SEQ ID NO: 5), fragment 2 (WKLNTGRTEAC) (SEQ ID NO: 6) and fragment 8 (GPQDQGTYSC) (SEQ ID NO: 7).
Figure 4C:
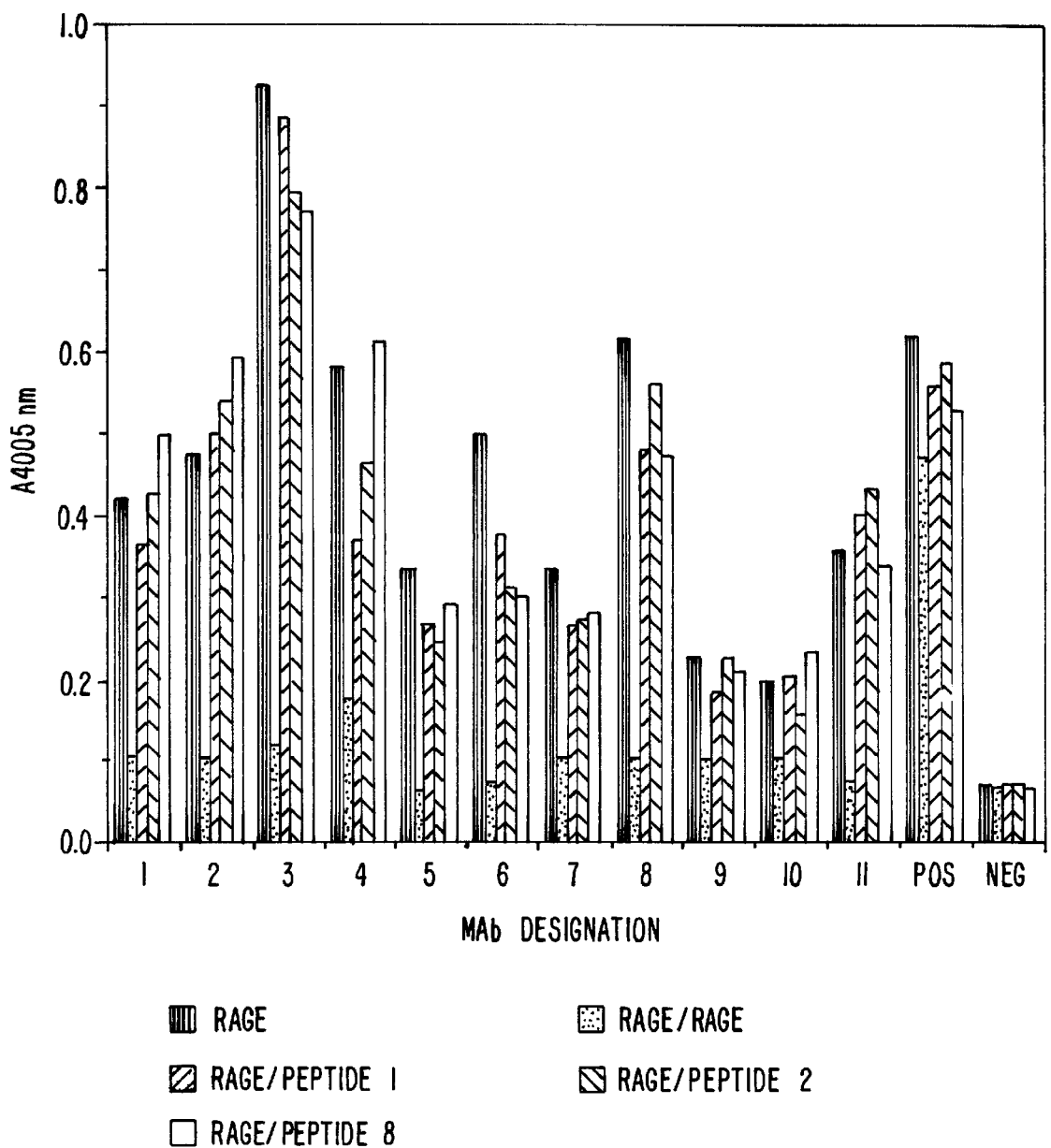

Eleven antibodies were also screened for binding to soluble human RAGE polypeptide fragments as compared to their binding to soluble human RAGE. FIG. 4B shows an antigen capture assay utilizing peptide fragment # 2 (WKLNTGRTEAC) (SEQ ID NO: 6). The 11 antibodies were also tested for binding to immobilized RAGE in the presence and absence of free soluble RAGE or RAGE polypeptide fragment # 1 (CKGAPKKPPQ) (SEQ ID NO: 5), fragment # 2 (WKLNTGRTEAC) (SEQ ID NO: 6) and fragment # 8 (GPQDQGTYSC) (SEQ ID NO: 7). The results are shown in FIG. 4C.

Figure 6A:
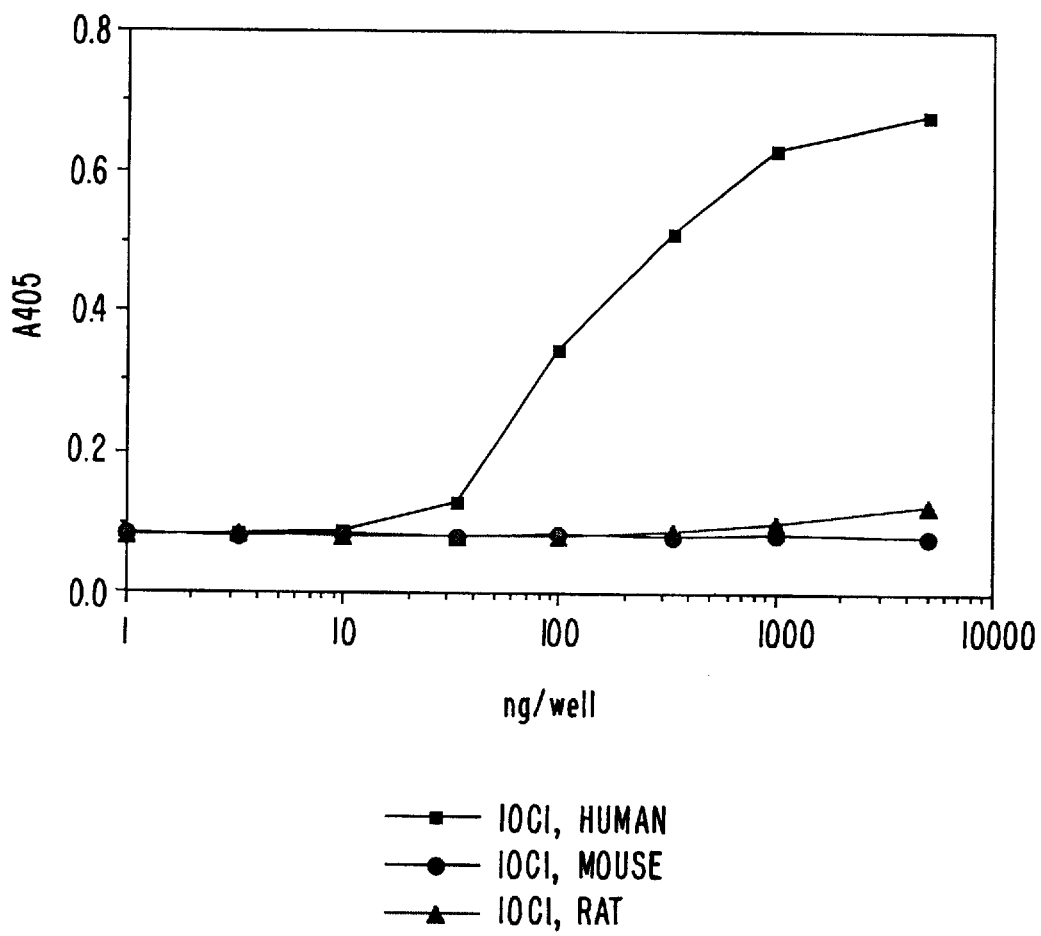
FIGS. 6A and 6B show results of a direct antigen capture EIA.

The sandwich EIA using MAbs RBF9D9 (ATCC Accession No. HB-12165) as capture and SW10C1-biotin (ATCC Accession No. HB-12165)as detection is specific for human RAGE, and does not cross react with either rat or mouse RAGE. This assay was used to detect and quantitate the presence of RAGE expressed in baculovirus, as well as CHO cells (FIG. 6A). Controls included a concentration range of purified RAGE for generation of a standard curve, as well as RAGE-spiked sera controls; the range of linearity is 20–100 ng/well.

Figure 5:
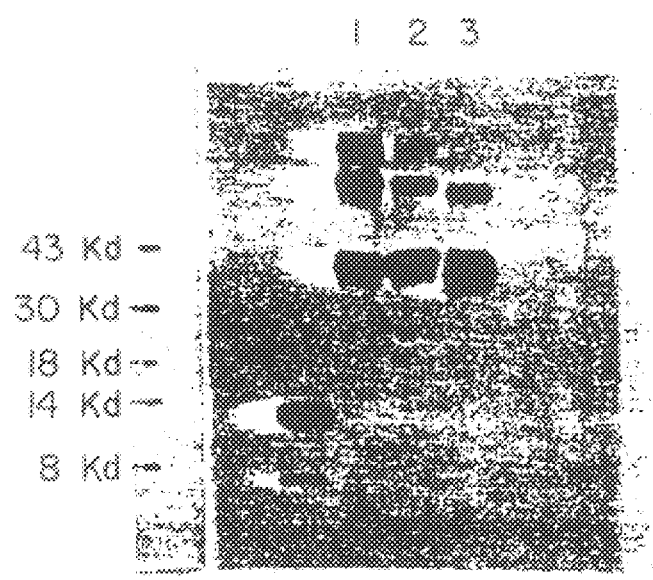
FIG. 5 shows a Western Blot hybridization of antiRAGE MAb SW1E8 (ATCC Accession No. HB-12166). Lanes 1–3 represent rat, mouse and human RAGE expressed in Baculovirus, respectively. Lanes were loaded with 5 μl of conditioned media. Monomeric RAGE is apparent as a doublet at approximately 41 Kd.
Figure 6B:
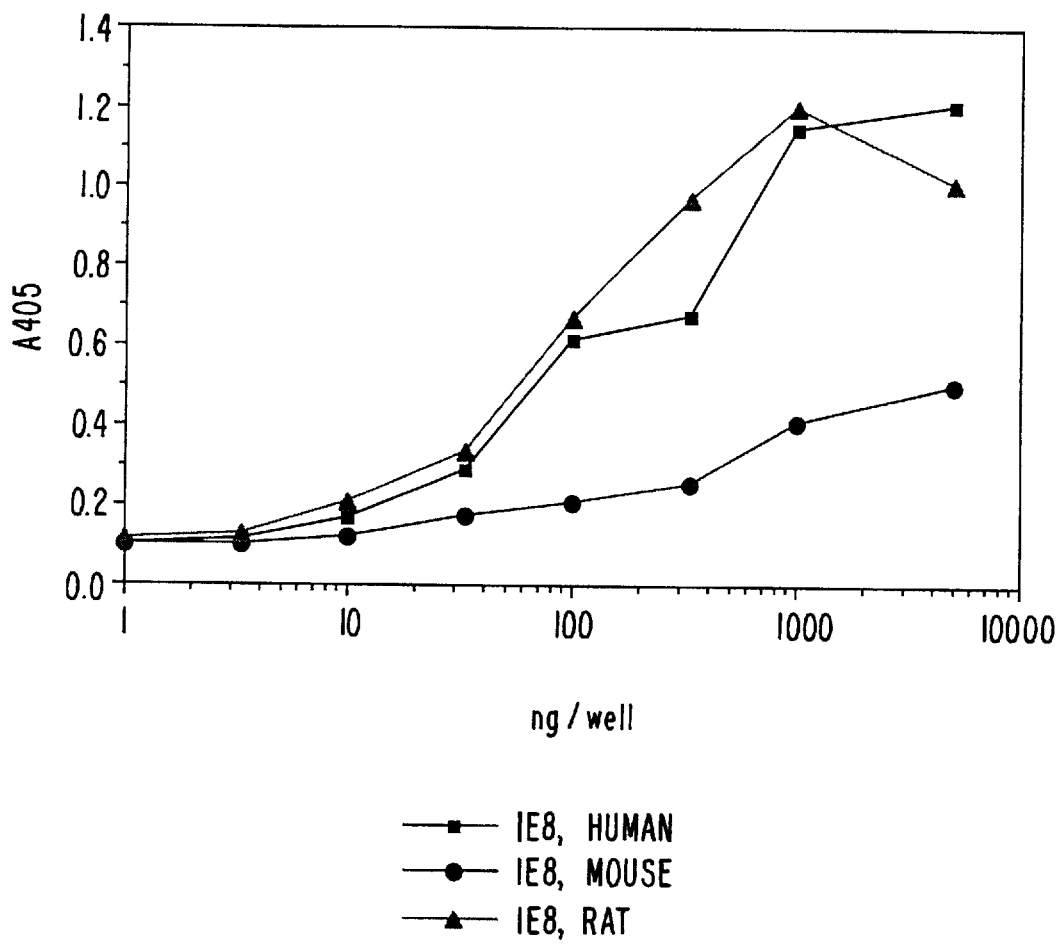

A second sandwich EIA, specific for human, rat, and mouse RAGE, uses MAbs RBF9D9 (ATCC Accession No. HB-12165) as capture and SW1E8-biotin (ATCC Accession No. HB-12166) as detection. This assay was used to detect and quantitate recombinant RAGE expressed in insect and mammalian cells (FIG. 6B), and sera obtained from lean and obese rats (not shown), including controls as above. Western blot analysis of the antibodies confirms reactivity to RAGE as shown in FIG. 5.

Figure 7:
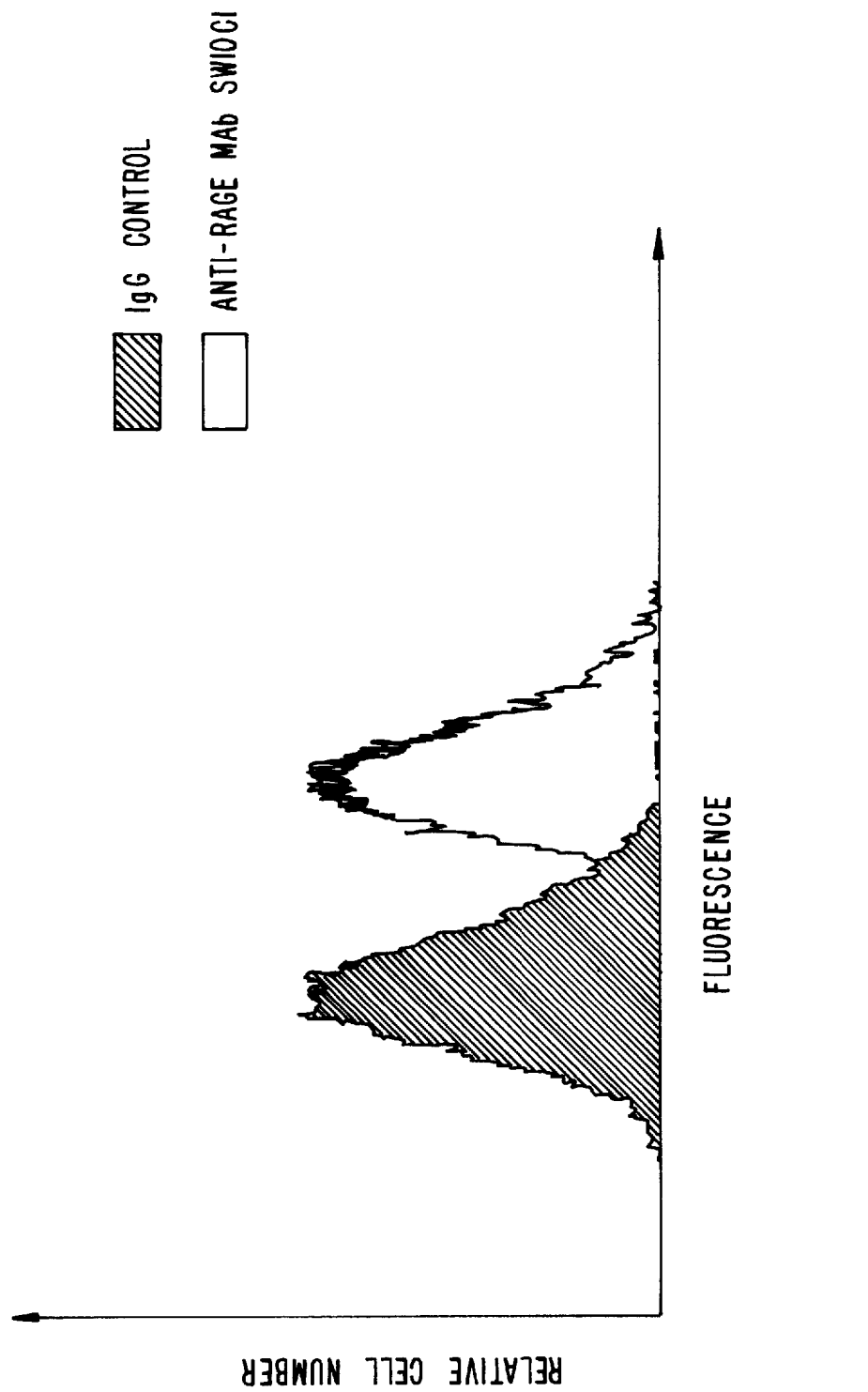
FIG. 7 shows the results of flow cytometry of CHO parental cells and CHO cells transfected with full length human RAGE, using anti-RAGE MAb SW1OC1. Sixty nine of the original 72 MAb panel demonstrated similar reactivity with cell surface RAGE.

Sixty-nine of the 72 anti-RAGE MAbs were positive for binding to cell surface RAGE, as determined by direct immunofluorescent staining of CHO-RAGE transfectant cells. Data from one binding experiment is shown in FIG. 7. The other 68 binding MAbs showed similar results. Additional FACS experiments included direct immunofluorescent staining of cells with anti-RAGE MAbs SW10C1 (ATCC Accession No. HB-12164), SW1E8 (ATCC Accession No. HB-12166), and RBF9D9 (ATCC Accession No. HB-12165), all of which strongly recognize cell surface RAGE. All three cell lines were deposited on Aug. 6, 1996 at the American Type Culture Collection (ATCC), 10801 University Boulevard, Manassas, Va. 20112-2209.

Figure 8:
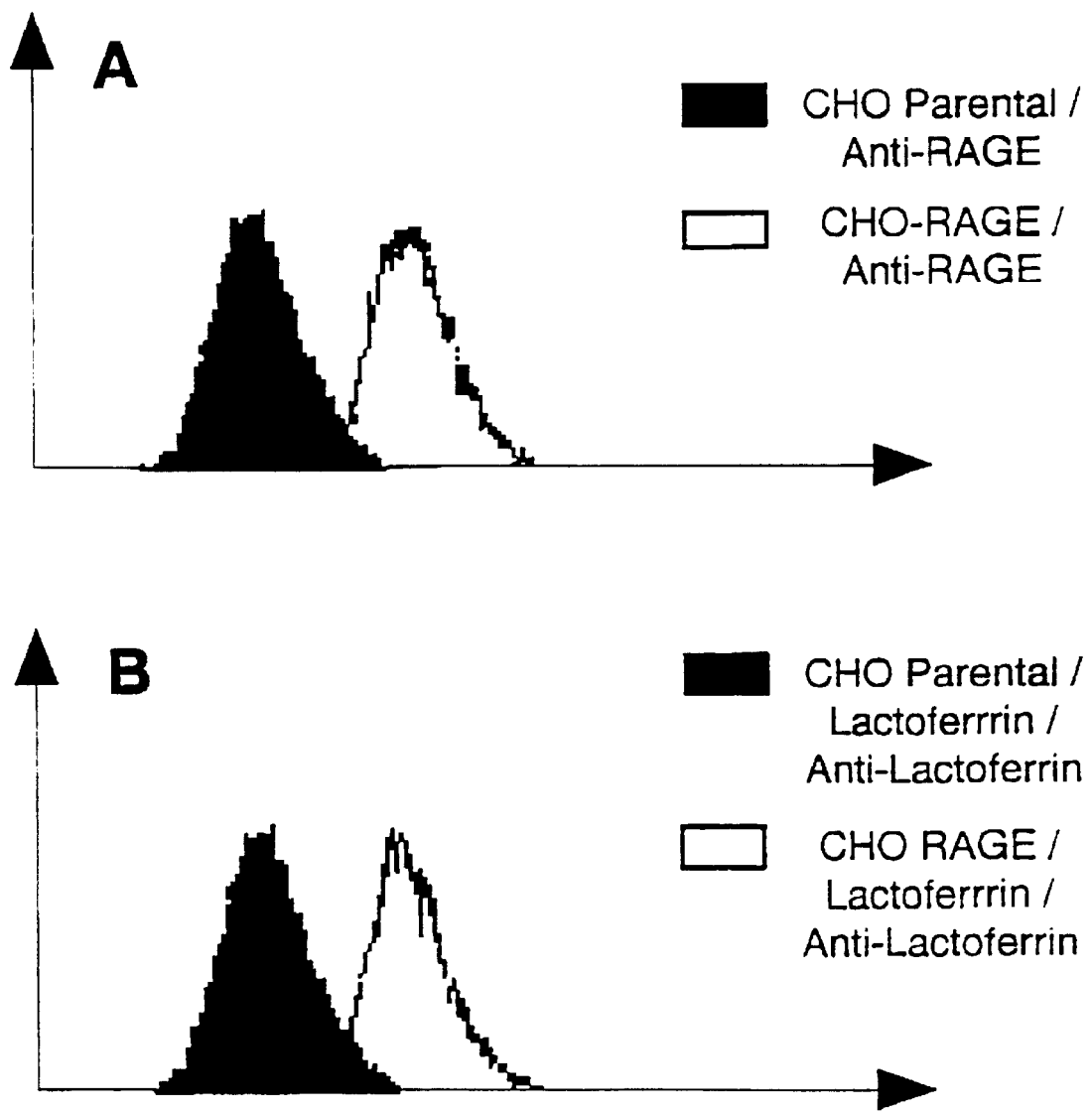
FIGS. 8A and 8B show results of flow cytometry of CHO parental and CHO-RAGE transfectants incubated with lactoferrin and immunostained with anti-RAGE/phycoerythrin (FIG. 8A) and anti-lactoferrin/FITC (FIG. 8B).

Binding of exogenous lactoferrin, however, was clearly demonstrated on the CHO-RAGE transfectants as shown in FIG. 8B. In particular, parental and RAGE transfected CHO cells were separately incubated with 5 μg lactoferrin and stained with both anti-RAGE/phycoerythrin and anti-lactoferrin/FITC. Phycoerythrin fluorescence shown in FIG. 8A, indicates the presence of RAGE on the cell surface. FITC fluorescence shown in FIG. 8B indicates the binding of lactoferrin to CHO-RAGE transfectants, but not to parental CHO cells.

Epitope analysis: The results of competition experiments, binding to the deletion mutant, and binding to rat and mouse RAGE clearly indicate that the panel of MAbs recognize unique and discrete antigenic determinants. Four MAbs recognize epitopes on the second or third Ig-like domains. One of these four recognizes an epitope that is exposed on the extracellular RAGE, but not cell surface RAGE, perhaps due to proximity to the cell surface. The remaining 69 MAbs recognize epitopes on the first Ig-like domain, and bind to at least four different sites on this domain.

EXAMPLE 5:

Effects of Soluble RAGE on Vascular Permeability

Early changes in vascular permeability are widely recognized as a hallmark of diabetic vascular dysfunction. As a result, the effect of recombinant soluble RAGE was tested in permeability models. See, e.g., Vlassara et al., Laboratory Invest. 70(2):138–151 (1994), Vlassara et al., Proc. Nat'l Acad. Sci. USA 91:11704–11708 (1995).

A. In vitro permeability studies

Bovine aortic endothelial cells (BAEC) were cult-Cured to confluency on nucleopore membranes. Seven days after reaching confluency, cells were incubated for 24 hours with red blood cells (RBCs) isolated from either normal subjects or diabetic patients. Endothelial cells were washed and permeability was measured in a permeability chamber containing minimal essential medium containing 10% fetal calf serum by adding $^{125}$I-albumin or $^{3}$H-inulin to the upper chamber. The emergence of radioactivity in the lower chamber was then measured over 24 hours at 37° C. Aliquots of medium (5µl) were sampled from the upper and lower chambers every 10 minutes for the first hour and at 1, 2, 4 and 24 hour time points to determine a permeability coefficient.

To determine the effect of recombinant soluble RAGE on in vitro permeability, normal or diabetic RBCs were first incubated with recombinant RAGE or control proteins (VCAM-1)(30 µg/ml) before adding to the endothelial cells.

Determination of permeability coefficient (P) was carried out by the following calculation:

$$P=(J)(1/A)(1/(C_t-C_b)$$

where J is the flux of molecules across the filter, A is the surface area of the confluent layer of endothelial cells, $C_t$ is the concentration of tracer in the upper chamber and $C_b$ is the concentration of tracer in the lower chamber. Post-confluent monolayers displaying permeability coefficients greater than $6.5 \times 10^{-7}$ cm/s, for albumin, or greater than $5 \times 10_{-6}$ cm/s for inulin were excluded.

Figure 9A:
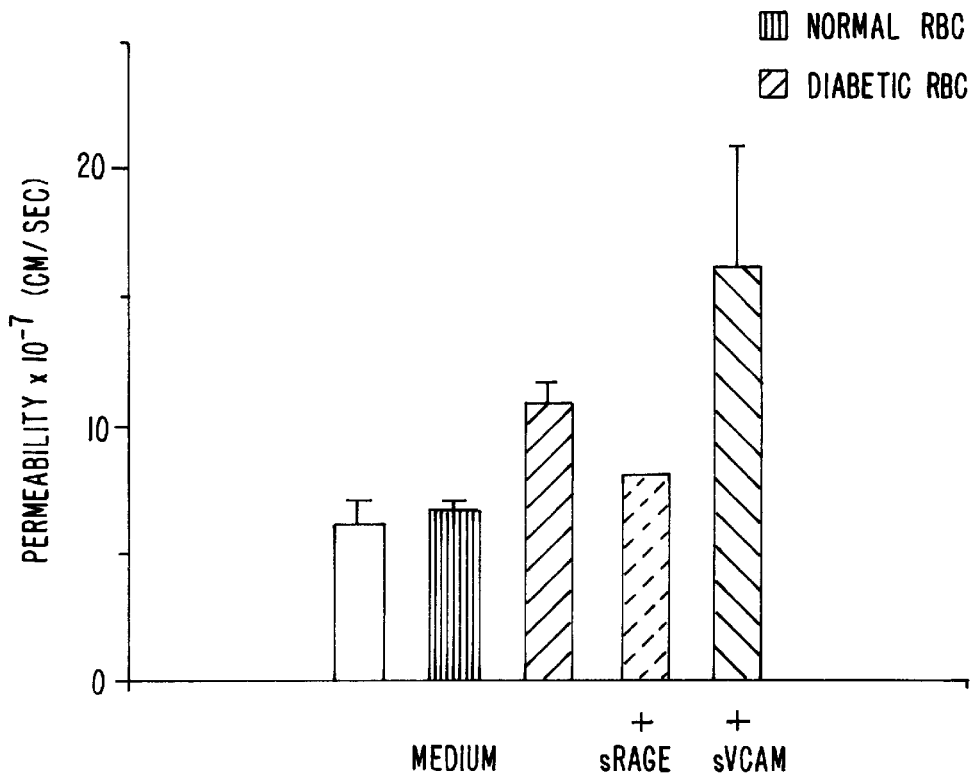
FIGS. 9A and 9B show the in vitro permeability of confluent BEAC layers by albumin and inulin. Permeability is shown following incubation with medium (control, white bar), normal RBCs (black bar) and diabetic RBCs (hatched bars). Reversal of diabetic RBC associated permeability is demonstrated following pretreatment with soluble recombinant RAGE (sRAGE) but not control protein (sVCAM).
Figure 9B:
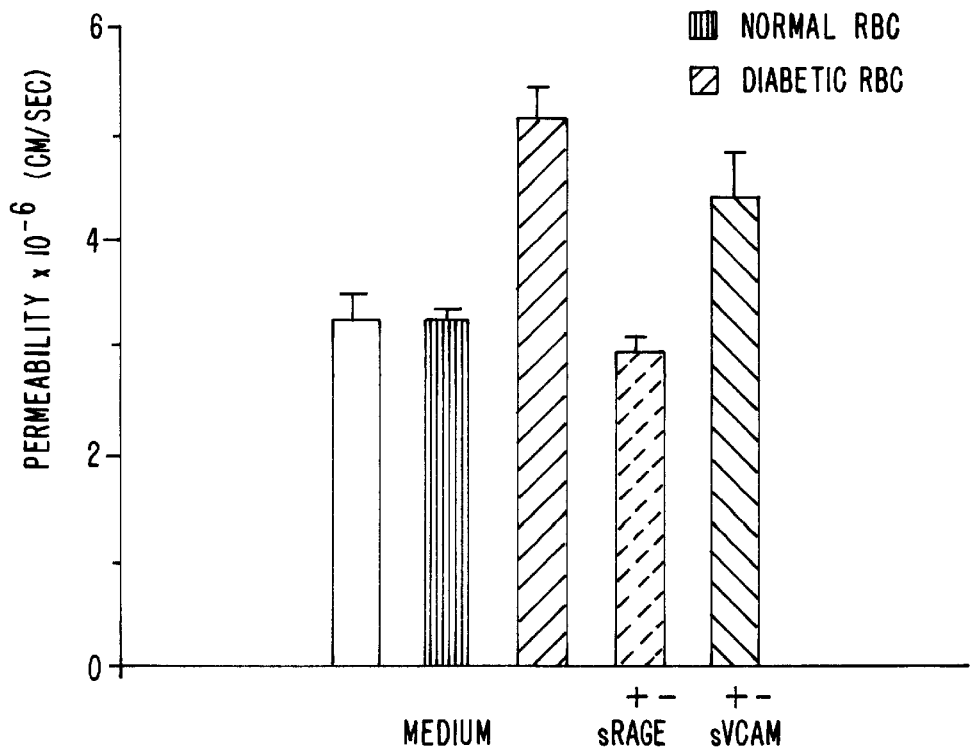

When endothelial cells were exposed to diabetic RBCs, the permeability of the monolayer to both macromolecules and micromolecules increased (FIG. 9A and 9B, respectively) compared with endothelial cells exposed to normal RBCs. This increased permeability was reversed by preincubation of diabetic RBCs with recombinant soluble RAGE, but not with the recombinant soluble control protein (VCAM-1, consisting of the first 3 Ig-like domains of VCAM-1 and having a structure similar to RAGE)(FIG. 9A and 9B).

B. TBIR (tissue-blood-isotope ratio) Studies

These studies were performed with normal and diabetic male Wister rats. Diabetes was induced in the rats by intravenous injection of streptozocin (45 mg/Kg) into animals weighing approximately 200 g. Animals were maintained for 9 to 11 weeks post-STZ prior to commencing the TBIR studies. Hyperglycemia (35–40 mmol/liter) was confirmed in diabetic rats.

RBCs were collected from normal or diabetic rats by puncturing the lower abdominal aorta. The RBCs were collected in a solution of dextrose (2.4%), citric acid (2.4%), sodium citrate (0.73%) and 2 parts anticoagulant to 8 parts blood. Blood was centrifuged to remove plasma and buffy coat, and the packed RBCs were washed and infused (4.2× 10⁹ cells/animal) into normal syngeneic animals (vol. 0.5 ml). After one hour, TBIR was determined by infusion of $^{125}$I-albumin followed 30 minutes later by infusion of $^{51}$Cr-labelled normal RBCs. Tissue and blood samples were collected 5 minutes later.

To test the effect of recombinant soluble RAGE (and the recombinant control protein), normal or diabetic RBCs were pretreated with the recombinant proteins (60 µg/ml RBCS) prior to infusion. Six animals were used per group.

Figure 10:
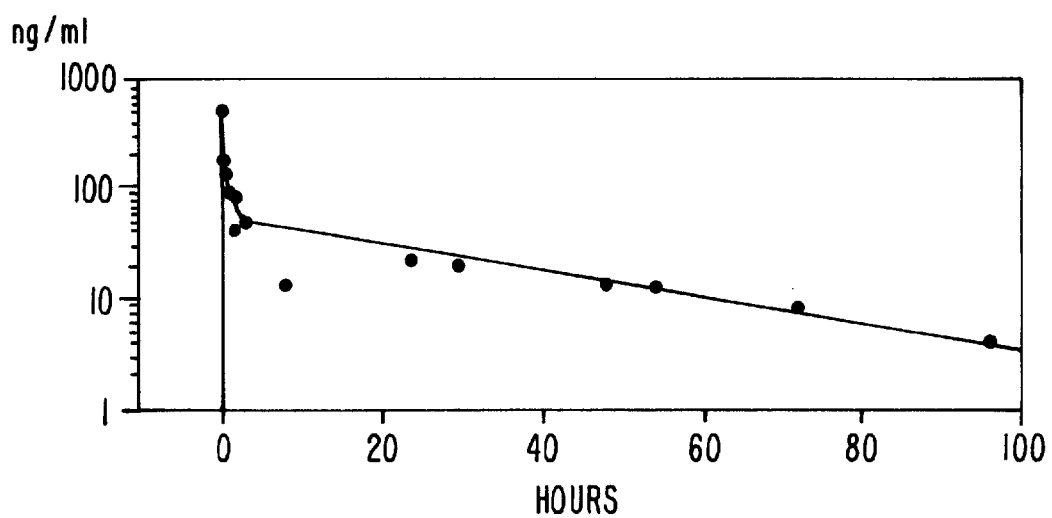
FIG. 10 shows plasma pharmacokinetics of $^{125}$I-human recombinant RAGE after an intravenous infusion into rat.

Pretreatment was carried out as follows: Diabetic rats were infused with either recombinant soluble RAGE or recombinant soluble VCAM-1 (control) (5.15 mg/Kg) 1 hour prior to TBIR measurement. In order to determine the dose of recombinant protein required to achieve a plasma concentration of 30 to 60 µg/ml, pharmacokinetic studies were performed using $^{125}$I-labelled recombinant soluble RAGE, the results of which are provided in FIG. 10. Radioactivity was measured as the trichloroacetic plasma precipitable fraction. Plasma human recombinant soluble RAGE concentration data were fit to a two compartment open model using nonlinear regression by extended least squares analysis (Siphar, SIMED, Cretail, France). The elimination and distribution half-lives were 26 and 0.13 hours, respectively. For TBIR studies, 10 control diabetic rats were used, 7 diabetic rats were treated with soluble RAGE and 5 rats were treated with the control protein.

TBIR was calculated as a ratio of $[^{125}I_,]/[^{51}Cr]$ in tissue over the same ratio in blood. One way analysis of variance followed by Dunnet's test was used to analyze the data for each organ. The results for normal and diabetic rats are given in FIGS. 12A and 12B, respectively.

Figure 11A:
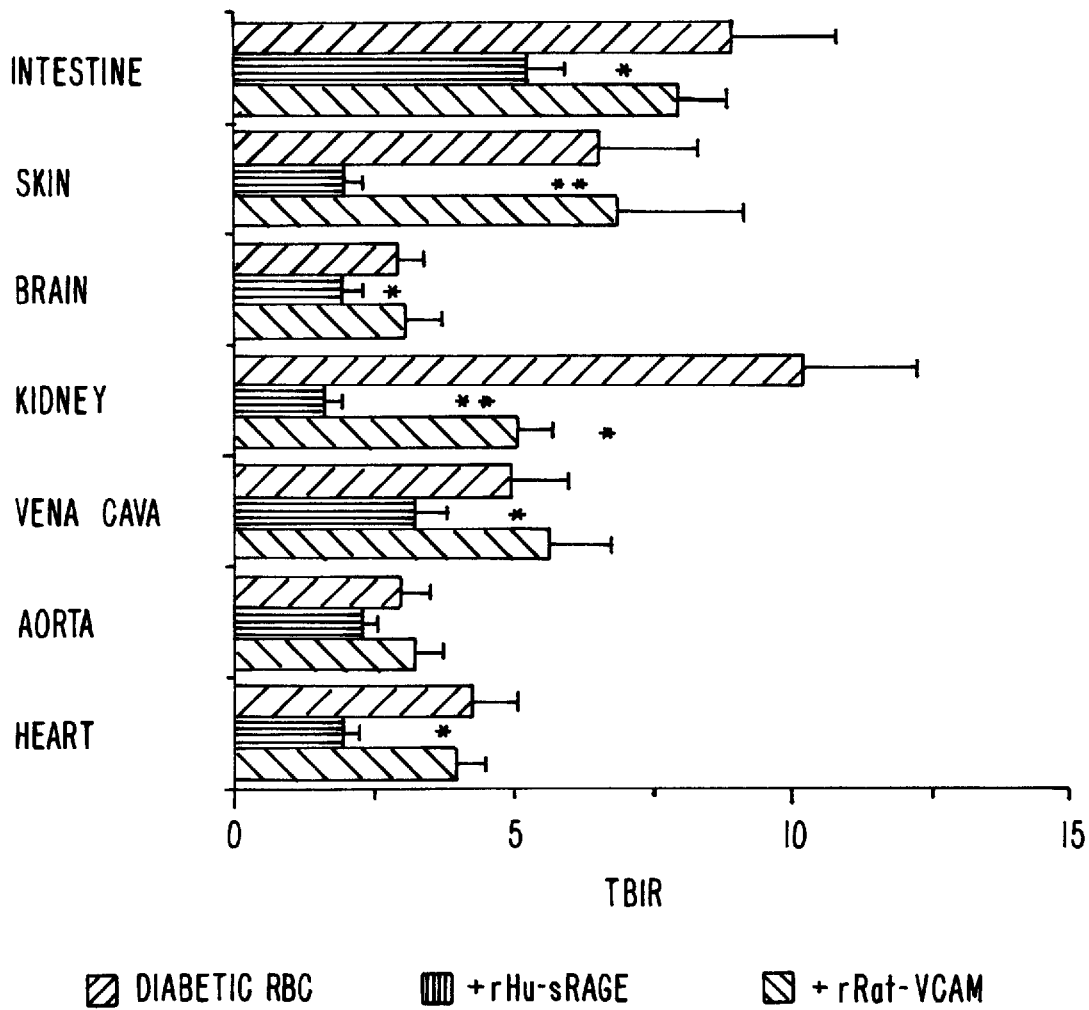
FIGS. 11A and 11B show comparisons of efficiency of recombinant soluble human RAGE and recombinant rat-VCAM in reversing permeability induced by diabetic RBC incubation in various tissues of normal (FIG. 11A) and diabetic rats (FIG. 11B).

In normal animals infused with diabetic RBCs, TBIR increased in a number of tissues as compared to infusion of normal RBCs (FIG. 11A). Most of the increases in TBIR were prevented by pretreatment of diabetic rats with recombinant soluble RAGE, but not with the control protein, with the exception of kidney tissue, which showed a similar effect with both RAGE and VCAM-1. These results indicate that AGEs on the surface of diabetic RBCs interact with surface RAGE on endothelial cells, triggering activation of the latter cells. This leads to an increased permeability of the endothelial layers. Without being bound to a particular theory, it is believed that pretreatment of diabetic RBCs with soluble RAGE prevents this interaction and, as a result, prevents increases in permeability as demonstrated.

Figure 11B:
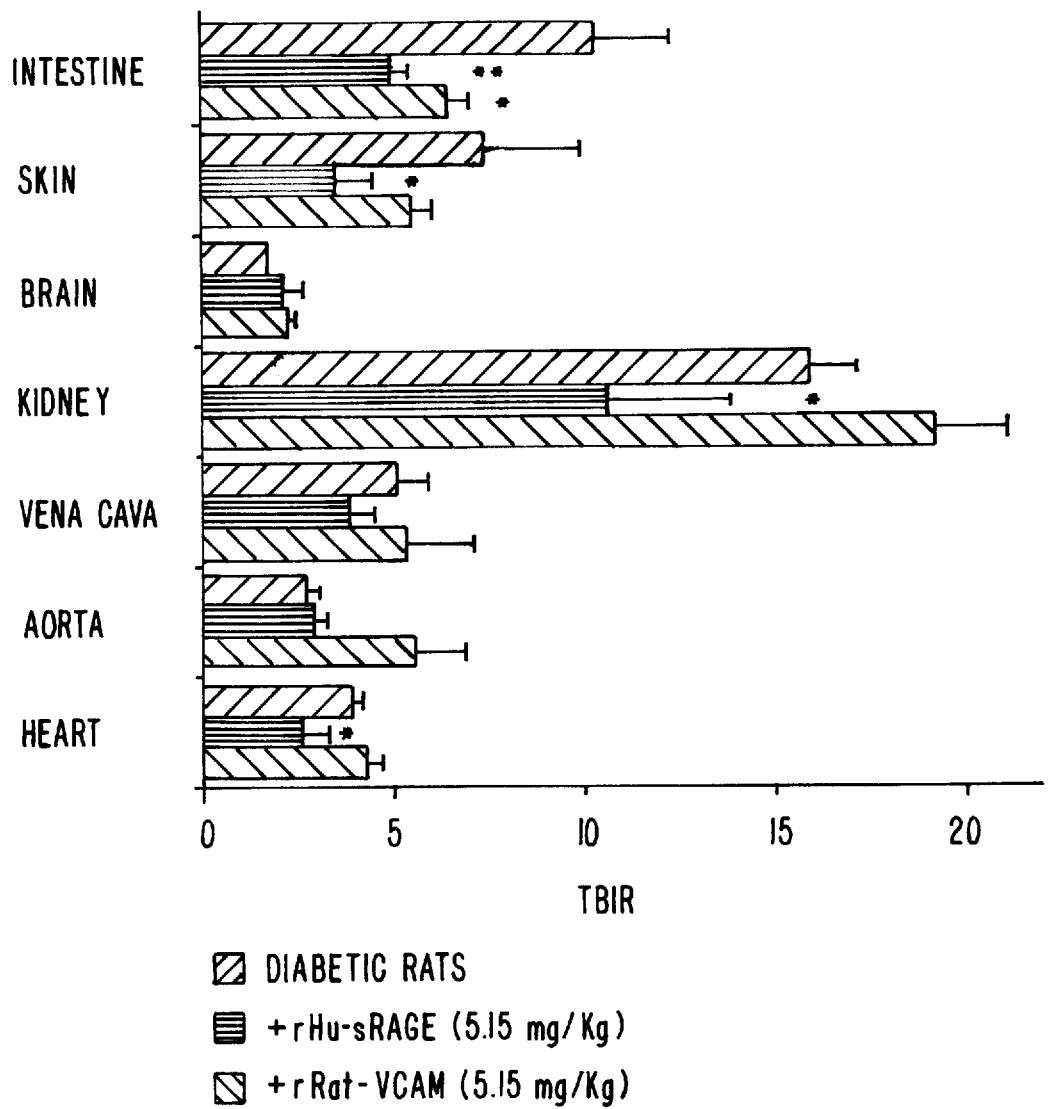

TBIR also increased in various tissues of diabetic rats as compared to those of normal rats. The increase in TBIR observed in some tissues, e.g., kidney, is reversed by acute administration of recombinant soluble RAGE. In other tissues, e.g., intestine, skin, both recombinant soluble RAGE and control protein had some effects (FIG. 11B). TBIR results in diabetic rats were not as clear as those for normal rats. This is believed to be a result of diabetes associated changes in hemodynamic factors that may effect TBIR. Accordingly, additional assays were performed to confirm the efficacy of RAGE in preventing diabetes associated increases in permeability.

C. Albumin Clearance Studies in STZ-induced Diabetic Rats

Young adult Sprague-Dawley rats (male, 6 weeks old, 150 g) were used. Diabetes was again induced by intravenous injection of streptozocin (65 mg/kg, available from Sigma Chemical Co.). Urine output and animal weight were monitored and blood samples collected weekly (tail clip sampling) for determination of serum glucose concentrations (glucose oxidase method). Animals rendered diabetic ([glucose]>30 mM) were used for experimental protocols.

Rats were anesthetized with isoflurane (1.5–2%) in the day of the experiment. Cannulae were placed in the jugular veins and left carotid artery. Five percent BSA (6 mg/Kg) was administered to compensate for fluid and protein losses during surgery. The animals were allowed to stabilize for 20–30 minutes prior to treatment.

For animals that received recombinant proteins, the following additional treatments were performed prior to infusion of a tracer: Recombinant soluble RAGE purified according to the methods described above was administered at infusion rates to achieve plasma concentrations of 60–80 µg/ml for 1.5 hours. Arterial pressure, right atrial pressure, and body temperature were continuously monitored. Western blotting was performed on plasma samples and standards to determine the level of circulating recombinant protein during the studies.

Figure 12:
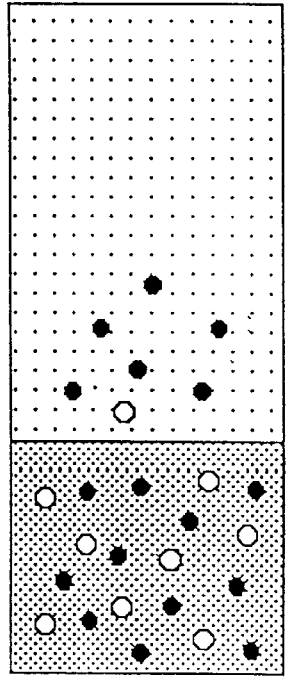
FIG. 12 shows a schematic illustration of the blood-tissue albumin transport tracer uptake method. Also shown are the calculations used to obtain albumin clearance values.

Albumin extravasation (albumin clearance, $C_{RSA}$) into individual tissues was calculated as the difference between the 35 minute $^{131}$I-RSA (rat serum albumin) (injected at t=0) and 5 minute $^{125}$I-RSA (injected at t=30 minutes) distribution volumes (See FIG. 12). A 30 minute clearance period was chosen in order to minimize loss of extravasated tracer from high permeability tissues (i.e., gut, kidney). Twenty tissue samples were surveyed in the studies: skin (hindlimb and back); skeletal muscle (gastrocnemius, tibialis anterior, abdominal wall); heart (left ventricle); lung (right and lefty lower lobe); lower trachea; aorta, sciatic nerve; retina; kidney; pancreas, jejunum, ileum, colon, testis, cerebrum and visceral fat pad. Initial and final plasma volumes were estimated as the 5 minutes $^{131}$I-RSA and $^{125}$I-RSA distribution volumes, respectively. Tissue extravascular water contents (EVW) were determiend as (wet weight)-($^{125}$I-RSA volume)-(dry weight). Values of CRSA and EVW were normalized to tissue blood-free dry weight. The data were separated into early (2–3 weeks), mid (4–10 weeks), and late (11–20 weeks) phases following streptozocin injection for comparison.

Figure 13A:
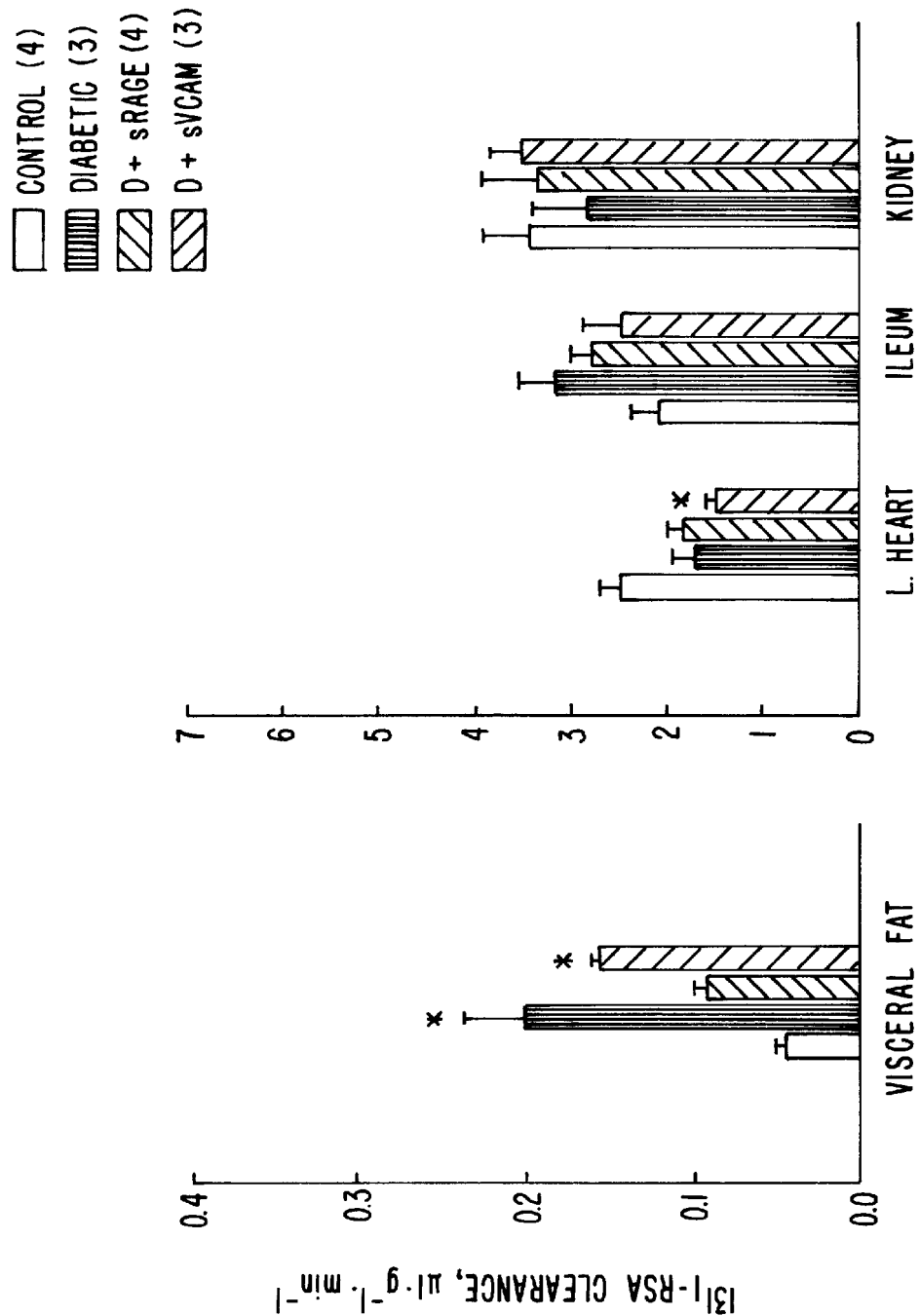
FIGS. 13A, 13B and 13C show albumin clearance from various tissues in control rats (white bar), diabetic rats (left black bar), diabetic rats with soluble RAGE pretreatment (middle black bar) and diabetic rats with soluble VCAM-1 pretreatment (right black bar) in early (FIG. 13A), mid (FIG. 13B) and late (FIG. 13C) phases of STZ-induced diabetes.
Figure 13B:
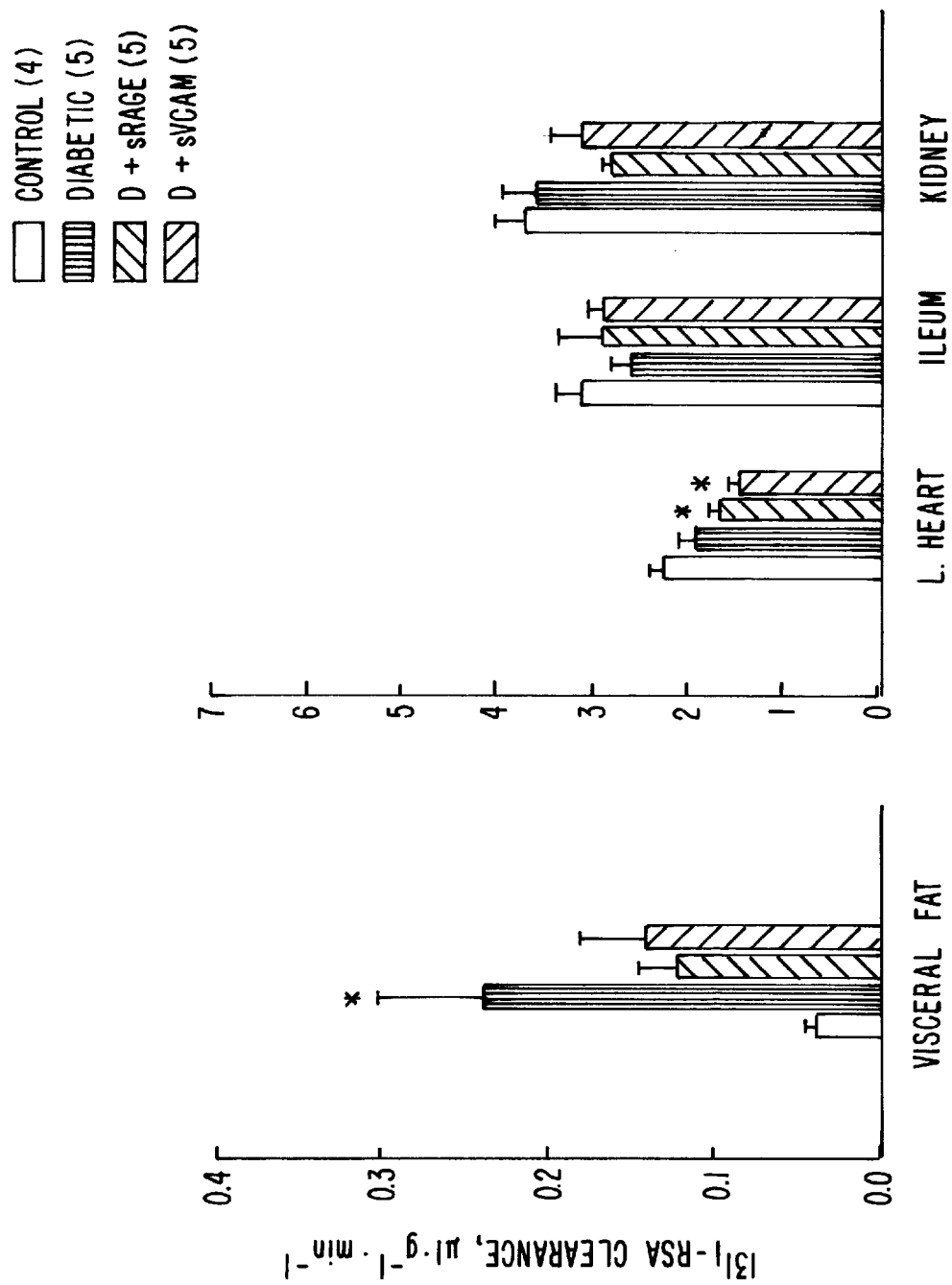
Figure 13C:
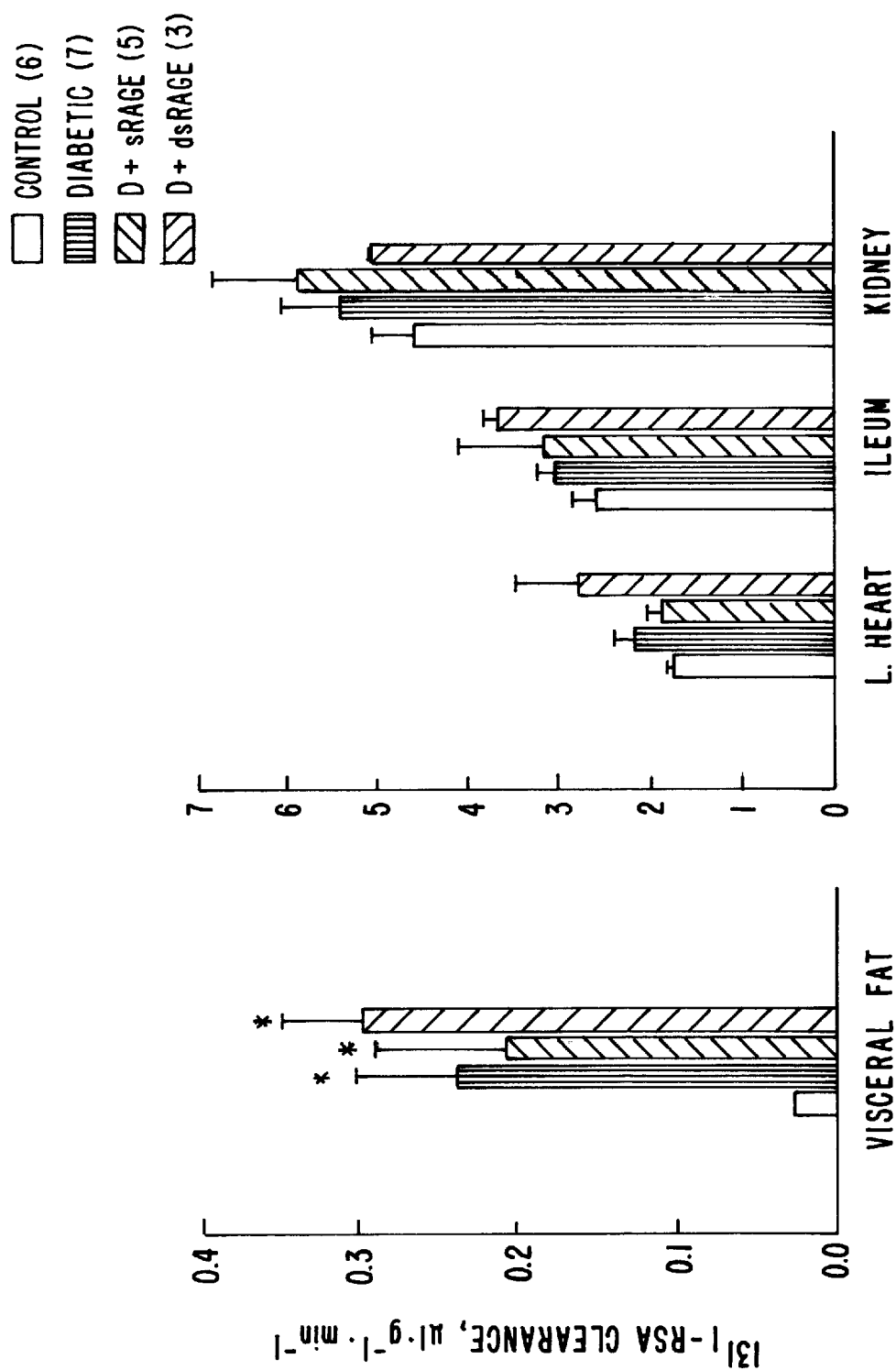

Regression analysis was performed on individual values of CRSA (over 30 minutes) plotted as a function of paired values of EVW. The slope of this relationship approximates the ratio of filtrate to plasma albumin concentration (i.e., the solvent drag coefficient). For hindlimb skin and skeletal muscles, the regression analyses were performed on differences in CRSA and EVW between paired hindlimbs (congested vs. non-congested). The results are shown in FIGS. 13A (early), 13B (mid) and 13C (late).

Figure 14A:
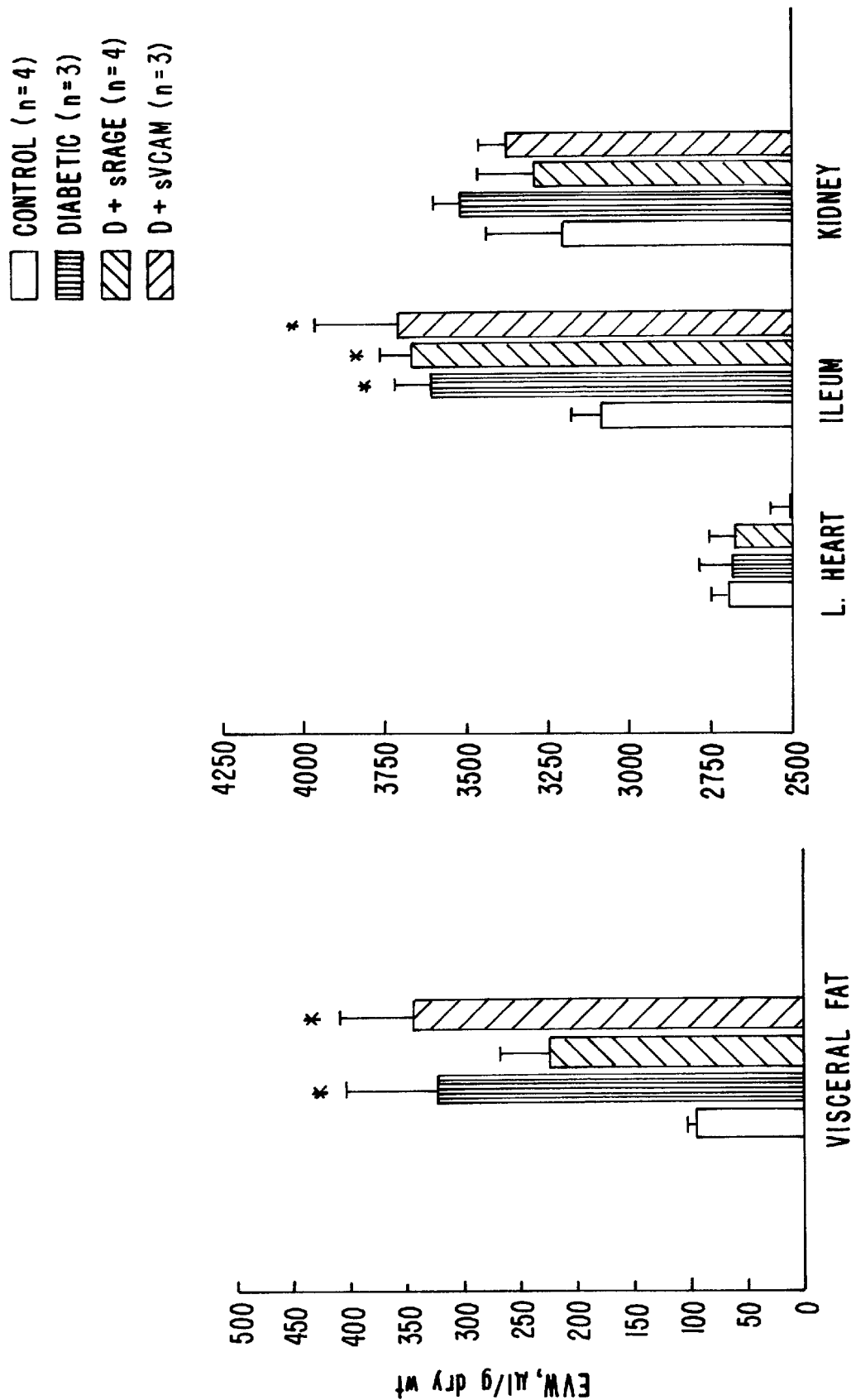
FIGS. 14A, 14B and 14C show extravascular water levels from various tissues in control rats (white bar), diabetic rats (left black bar), diabetic rats with soluble RAGE pretreatment (middle black bar) and diabetic rats with soluble VCAM-1 pretreatment (right black bar) in early (FIG. 14A), mid (FIG. 14B) and late (FIG. 14C) phases of diabetes.
Figure 14B:
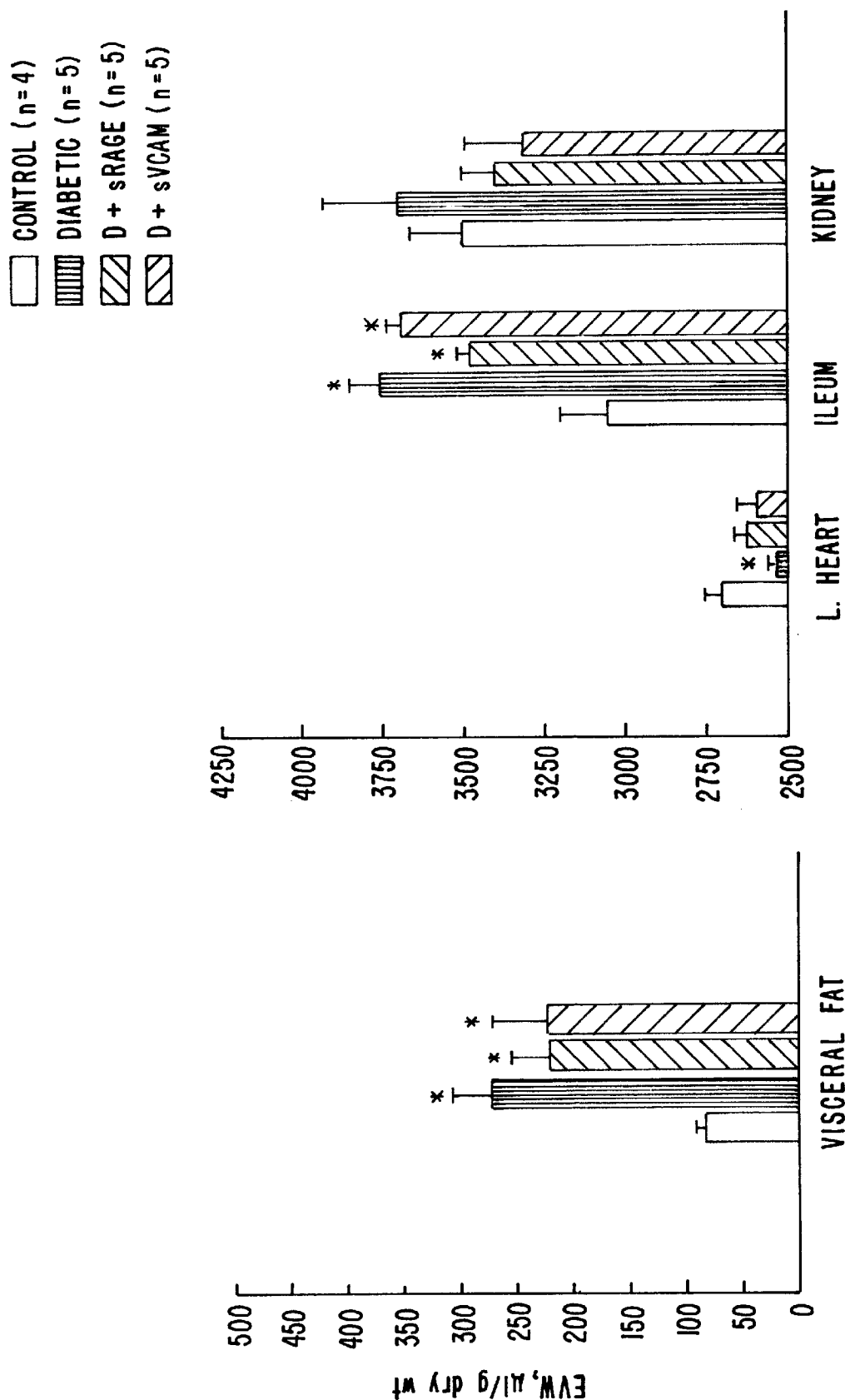
Figure 14C:
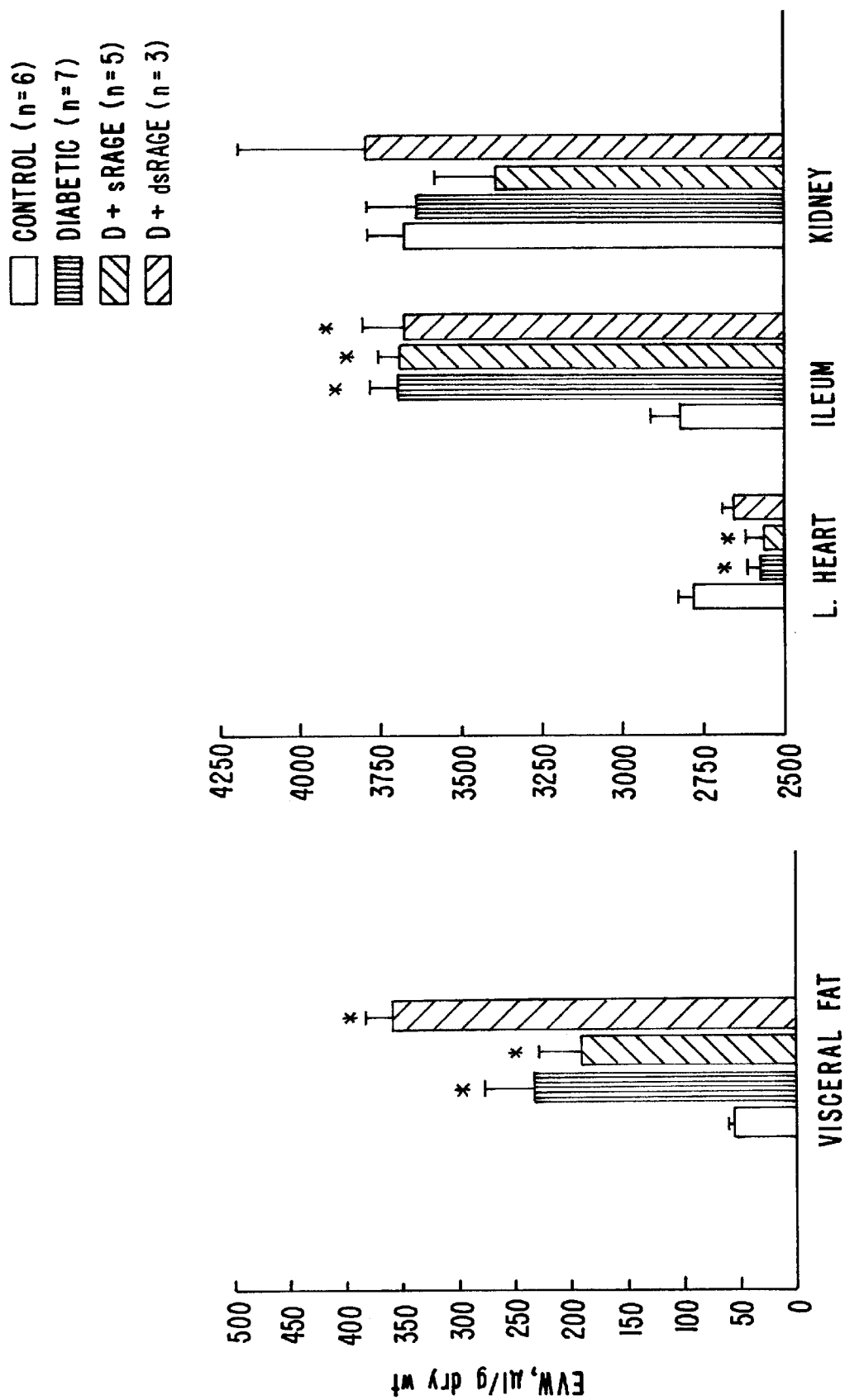

Over the 20 week "post-STZ treatment" period, there were increases in albumin clearance in visceral fat (+385%) in the early phase, and in skin (+75%), skeletal muscle (+68%) aorta (80%) and trachea (+84%) in the late phase. No differences in albumin clearance were apparant in intestine, kidney and heart tissue of diabetic rats compared with that of control rats. An intravenous administration of recombinant soluble RAGE (1 mg/Kg body weight) 1 hour prior to the clearance measurement shows some effect on reducing albumin clearance rates in visceral fat in early phase diabetes. Similar results were obtained for tissue extravascular water content per gram of dry weight (FIGS. 14A–C). Although not shown there were also indications that recombinant soluble RAGE reduced capillary pressure in diabetic rats.

D. Single Microvessel Studies

Figure 15B:
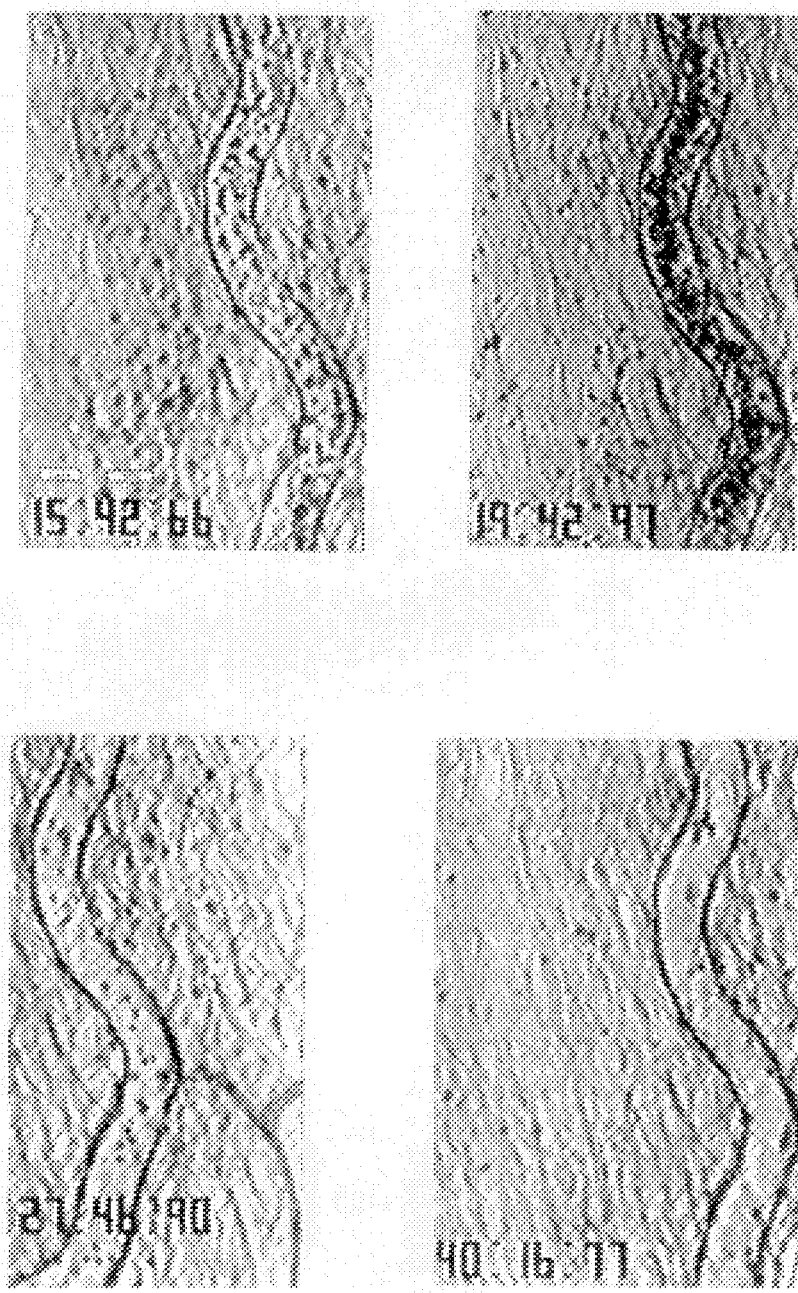

Normal rats were anesthetized with 1% and the ileal mesentary was exposed through a midline incision. The exposed gut was continuously superfused with mammalian Ringer's solution. Experiments were performed by cannulating a test vessel with control solution (5 mg/ml BSA and washed RBCs from normal rats or from diabetic rats in Ringer's solution) in the absence or presence of recombinant soluble RAGE, and examining the vessel for sticking red blood cells under a microscope. Examples of these vessels are shown in FIGS. 15A and 15B. Diabetic RBCs adhered to the venular wall when perfused into a normal rat vessel, whereas normal RBCs did not. Subsequent perfusion of diabetic RBCs and recombinant soluble RAGE into the same vessel did not result in further sticking of diabetic RBCs to the vessel wall. Perfusion of diabetic RBCs pretreated with recombinant soluble RAGE into the vessel from the same animal used previously did not result in adherence of RBCs to the vessel wall. Subsequent perfusion of diabetic RBCs (not pretreated with RAGE) did not result in adherence of the RBCs to the vessel wall.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. An isolated monoclonal antibody, wherein said antibody specifically binds to a soluble human receptor to an advanced glycosylation end-product ("RAGE") polypeptide and wherein the polypeptide consists of an amino acid sequence selected from the group consisting of: WKLNTGRTEA (SEQ ID No: 8); CEVPAQPSPQI (SEQ ID No: 9); CRAMNQNGKETKSN (SEQ ID No: 10); GPQDQGTYSC (SEQ ID No: 7); AQNITARIGEPLVLK (SEQ ID No: 12); CKGAPKKPPQ ( SEQ ID No: 5); EQTRRHPET (SEQ ID No: 14); RGGDPRPTFSC (SEQ ID No: 15); SPGLPRHRAL (SEQ ID No: 16); and SSHGPQESRA (SEQ ID No: 17).

2. An isolated monoclonal antibody said antibody specifically binds to a soluble human receptor to an advanced glycosylation end-product ("RAGE") polypeptide and wherein the polypeptide consists of an amino acid sequence selected from the group consisting of: WKLNTGRTEAC (SEQ ID No: 6); CKGAPKKPPQ (SEQ ID No: 5); and GPQDQGTYSC (SEQ ID No: 7).

3. The isolated antibody of claim 1, wherein said antibody is humanized.

4. The isolated antibody of claim 2, wherein said antibody is humanized.

5. The isolated antibody of claim 1, wherein said antibody further comprises a labeling group.

6. The isolated antibody of claim 5, wherein said labeling group is selected from the group consisting of a fluorescent label, a radioactive label and a bioactive label.

7. The isolated antibody of claim 2, wherein said antibody further comprises a labeling group.

8. The isolated antibody of claim 7, wherein said labeling group is selected from the group consisting of a fluorescent label, a radioactive label and a bioactive label.

9. A composition, comprising an antibody of claim 1 in combination with a pharmaceutically acceptable carrier.

10. A composition, comprising an antibody of claim 2 in combination with a pharmaceutically acceptable carrier.

* * * * *

UNITED STATES PATENT AND TRADEMARK OFFICE
CERTIFICATE OF CORRECTION

PATENT NO. : 5,864,018
DATED : January 26, 1999
INVENTOR(S) : Michael John Morser; Mariko Nagashima; Doris A. Hollander It is certified that error appears in the above-identified patent and that said Letters Patent is hereby corrected as shown below:

On the title page , item [75] Inventors:

Line 2, after "Belmont" delete "both of Calif." and insert --; Doris A. Hollander, Orinda, all of California.--

Signed and Sealed this

Fifteenth Day of June, 1999

Attest:

Q. TODD DICKINSON

Attesting Officer

Acting Commissioner of Patents and Trademarks